US012588814B2

(12) United States Patent
Fenster

(10) Patent No.: US 12,588,814 B2
(45) Date of Patent: Mar. 31, 2026

(54) VISION SCREENING DEVICE INCLUDING OVERSAMPLING SENSOR

(71) Applicant: Welch Allyn, Inc., Skaneateles Falls, NY (US)

(72) Inventor: Douglas Paul Fenster, Onondaga Hill, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 341 days.

(21) Appl. No.: 18/211,027

(22) Filed: Jun. 16, 2023

(65) Prior Publication Data

US 2023/0404397 A1      Dec. 21, 2023

Related U.S. Application Data

(60) Provisional application No. 63/352,695, filed on Jun. 16, 2022.

(51) Int. Cl.
*A61B 3/14*          (2006.01)
*A61B 3/11*          (2006.01)

(52) U.S. Cl.
CPC ................ *A61B 3/14* (2013.01); *A61B 3/111* (2013.01)

(58) Field of Classification Search
CPC ....... A61B 3/0025; A61B 3/111; A61B 3/113; A61B 3/14; A61B 3/152
See application file for complete search history.

(56) References Cited

U.S. PATENT DOCUMENTS 6,089,715 A    7/2000  Hoover et al.
6,419,638 B1   7/2002  Hay et al.
6,611,613 B1   8/2003  Kang et al.
6,873,714 B2   3/2005  Witt et al.
6,926,429 B2   8/2005  Barlow et al.
(Continued)

FOREIGN PATENT DOCUMENTS

WO    WO2021092211 A1    5/2021
WO    WO2021217218 A1    11/2021

OTHER PUBLICATIONS

PCT Search Report and Written Opinon mailed Sep. 28, 2023 for PCT Application No. PCT/US23/25612, "Vision Screening Device Including Oversampling Sensor", 10 pages.
(Continued)

*Primary Examiner* — Nelson M Rosario

(74) *Attorney, Agent, or Firm* — Lee & Hayes, P.C.

(57) ABSTRACT

A vision screening device for administering vision screening tests to a patient, including an oversampling sensor allowing operation of the device at various distances from a patient, is described herein. The vision screening device may include associated methods and systems configured to capture a series of oversampled images, detect the patient's face and eyes in the images, track the eyes, and output a stabilized eye image for performing the vision screening tests. The device may also be configured to determine measurements related to the positions of the eyes in the eye image, and determine, based on the measurements, if the eye image satisfies criteria for use in the vision screening tests being performed. Methods associated with the device may be configured to provide guidance to an operator of the device to adjust either the device or the patient's position so that an eye image meeting the criteria can be generated.

20 Claims, 7 Drawing Sheets

(56) References Cited

U.S. PATENT DOCUMENTS

| 9,408,535 | B2 | 8/2016 | Mowrey et al. | |
|---|---|---|---|---|
| 9,642,523 | B2 | 5/2017 | Cleveland | |
| 10,194,799 | B2 | 2/2019 | Gerrans | |
| 10,506,924 | B2 | 12/2019 | Thompson et al. | |
| 10,713,483 | B2 | 7/2020 | Creedon et al. | |
| 2008/0143854 | A1 | 6/2008 | Steinberg et al. | |
| 2013/0235346 | A1* | 9/2013 | Huang ................... | A61B 3/152 |
| | | | | 351/208 |
| 2014/0285768 | A1* | 9/2014 | Barnard ............... | G06V 40/193 |
| | | | | 382/195 |
| 2016/0271002 | A9 | 9/2016 | Simmons | |
| 2023/0005144 | A1* | 1/2023 | Shin ....................... | G16H 50/30 |

OTHER PUBLICATIONS

Zheng, et al, "Intelligent Evaluation of Strabismus in Videos Based on an Automated Cover Test", MDPI, Applied Sciences 2019, 9, 731, retrieved from <<www.mdpi.com/journal/applsci>>, pp. 1-16.

* cited by examiner

400 ⟶

CAPTURE OVERSAMPLED IMAGE 402

IDENTIFY A FACE OF A PATIENT IN THE OVERSAMPLED IMAGE 404

IDENTIFY A FIRST EYE AND A SECOND EYE OF THE PATIENT 406

DETERMINE POSITIONS OF THE FIRST EYE AND THE SECOND EYE 408

POSITIONS SATISFY CRITERIA FOR EYE IMAGES? 410

No

NOTIFY OPERATOR 412

YES

GENERATE EYE IMAGE 414

DETERMINE CONDITION OF FIRST EYE OR SECOND EYE 416

OUTPUT AN INDICATION OF THE CONDITION 418

1

VISION SCREENING DEVICE INCLUDING OVERSAMPLING SENSOR

CROSS REFERENCE TO RELATED APPLICATION

This application is a Nonprovisional of, and claims priority to U.S. Provisional Patent Application No. 63/352,695, entitled "VISION SCREENING DEVICE INCLUDING OVERSAMPLING SENSOR," filed on Jun. 16, 2022, the entirety of which is incorporated herein by reference.

TECHNICAL FIELD

This application is directed to medical equipment. In particular, this application is directed to a vision screening device, and associated systems and methods, for administering vision screening tests while accommodating variations in distance from the patient and patient movement.

BACKGROUND

Vision screening typically includes screening tests for various diseases and deficiencies of the eye. Such vision screening tests may include, for example, refractive error tests, accommodation tests, visual acuity tests, color vision screening, screening for diseases of the retina and ocular media, and the like. The vision screening tests may be administered using a vision screening device, which may be of a compact and/or portable design (e.g., a handheld device, a mobile device similar to a tablet or a smartphone, etc.) to allow for testing at any location, from conventional screening environments, such as schools and medical clinics, to physician's offices, hospitals, eye care facilities, and/or other remote and/or mobile locations.

The screening tests may have respective distance requirements or other parameters that must be met in order to ensure accurate testing results. For example, an ideal distance between the patient and the vision screening device during the administration of a vision screening test may vary from approximately three feet to approximately twenty-two feet in some instances. Due to the narrow field of view of a typical vision screening device, it may be difficult for an operator of the vision screening device to locate and center the patient's eyes in a viewfinder or screen of the device, especially at distances above three feet. In addition, the effect of jitter caused by small movements arising from the operator hand-holding the vision screening device while administering the vision screening test(s) or slight movement of the patient is also amplified at distances above three feet, and imaging components of the vision screening device may not be able to acquire sharp images of the eyes, and parts of the eyes, and keep the eyes centered in the images, as required for the screening tests.

Accordingly, it would be advantageous for a vision screening device to be configured to operate at various distances from the patient, and achieve proper centering and stabilized imaging of the eyes for accurate administration of vision screening test(s).

The various examples of the present disclosure are directed toward overcoming one or more of the deficiencies noted above.

SUMMARY

In an example of the present disclosure, vision screening device includes a sensor (e.g., an oversampling sensor) configured to capture an image, a processor operably connected to the sensor, and memory storing instructions executable by the processor. The instructions when executed, cause the processor to cause the sensor to capture a first image of an environment including a patient, identify a first portion of the first image corresponding to a face of the patient, determine, based on the first portion, a second portion of the first image disposed at least partially within the first portion, wherein the second portion illustrates a first eye of the patient and a second eye of the patient, determine a first position of the first eye within the second portion, and a second position of the second eye within the second portion, and determine whether the first position and the second position satisfy respective eye position criteria. The instructions, when executed, also cause the processor to extract image data from the first image, based on determining that the first position and the second position satisfy the respective eye position criteria, wherein the image data includes data corresponding to the second portion, and excludes data corresponding to a remainder of the first image outside of the second portion, and generate, based on the image data, a second image illustrating the first eye and the second eye.

In another example of the present disclosure, a method includes capturing a first image, the first image including a patient, identifying a first portion of the first image, the first portion illustrating at least part of a face of the patient, identifying a second portion of the first image disposed at least partially within the first portion, wherein the second portion illustrates a first eye of the patient and a second eye of the patient, and determining, based on the second portion and relative to a center point of the first portion, a first position of a pupil of the first eye and a second position of a pupil of the second eye. The method also includes determining whether the first position and the second position satisfy respective pupil position criteria, and based on determining that the first position and the second position satisfy the respective pupil position criteria, extracting image data from the first image, wherein the image data includes data corresponding to the second portion, and excludes data corresponding to a remainder of the first image outside of the second portion. The method further includes generating, based on the image data, a second image illustrating the first eye and the second eye, determining, based on the second image, a condition of at least one of the first eye or the second eye, and outputting an indication of the condition via an electronic device.

In still another example of the present disclosure, a system includes memory, a processor, and computer-executable instructions stored in the memory and executable by the processor. The instructions, when executed, cause the processor to perform operations comprising: causing a sensor to capture a first image of a patient, determining a first portion of the first image corresponding to a face of the patient, determining a second portion of the first image having a boundary disposed at least partially within the first portion, wherein the second portion illustrates a first eye of the patient and a second eye of the patient. The instructions, when executed, also cause the processor to determine a first position of the first eye relative to the boundary of the second portion, and a second position of the second eye relative to the boundary of the second portion, determine whether the first position and the second position satisfy respective eye position criteria, and based on determining that the first position and the second position satisfy the respective eye position criteria, extracting image data from the first image, wherein the image data excludes data, of the first image, from outside of the boundary. The instructions, when executed, further cause the processor to generate, based on the image data, a second image illustrating the first eye and the second eye, and determine, based on the second image, a condition of at least one of the first eye or the second eye.

BRIEF DESCRIPTION OF THE DRAWINGS

Features of the present disclosure, its nature, and various advantages, may be more apparent upon consideration of the following detailed description, taken in conjunction with the accompanying drawings.

In the figures, the left-most digit(s) of a reference number identifies the figure in which the reference number first appears. The use of the same reference numbers in different figures indicates similar or identical items or features. The drawings are not to scale.

DETAILED DESCRIPTION

Figure 1:
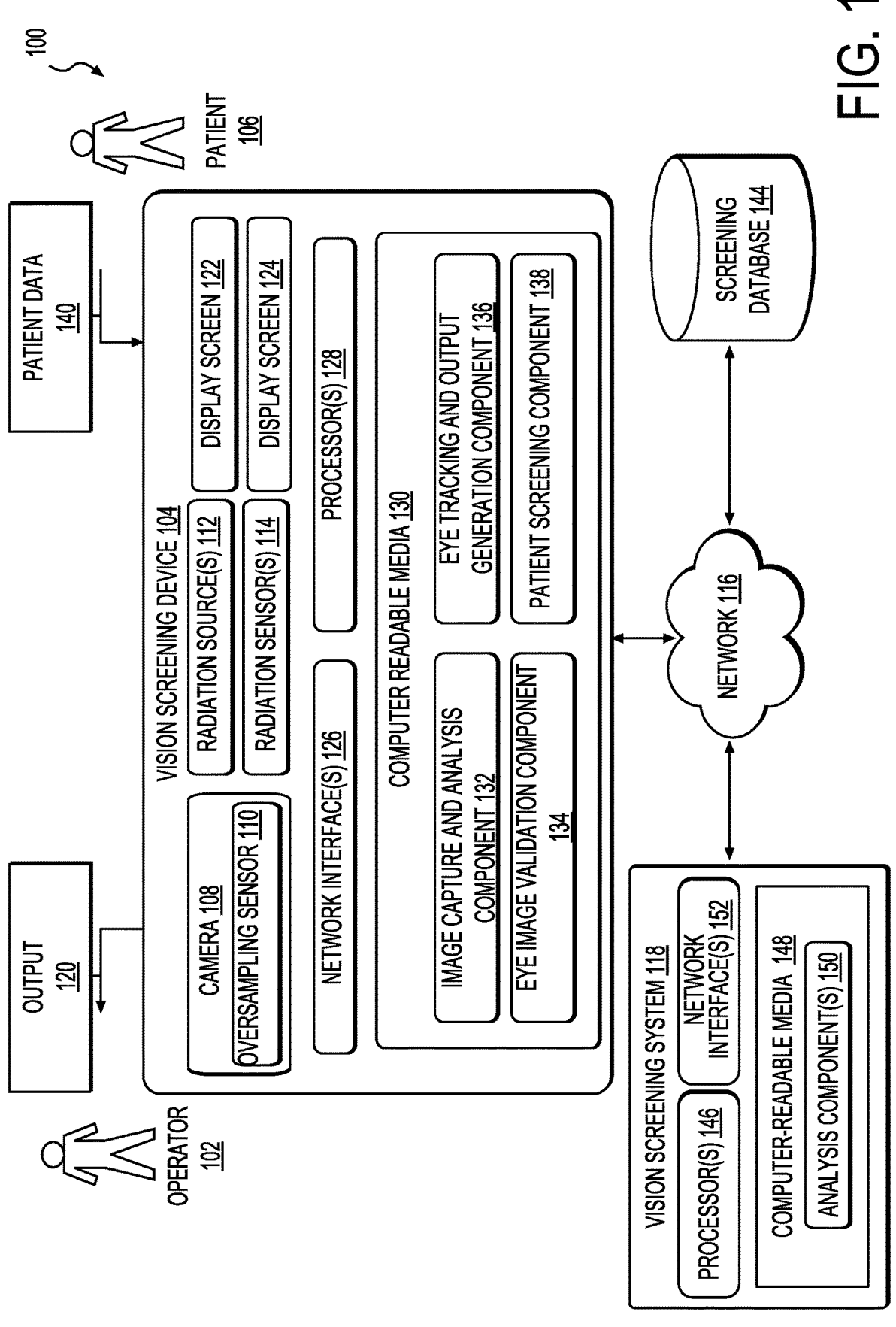
FIG. 1 illustrates an example vision screening device and vision screening system of the present disclosure. In some implementations, components of the example system shown in FIG. 1 may be used to perform one or more screening tests associated with vision screening and/or detection of diseases or deficiencies of the eyes.

The present disclosure is directed to, in part, a vision screening device, and corresponding methods. Such an example vision screening device may be configured to perform one or more vision screening tests on a patient and to output the results of the vision screening test(s) to an operator of the device, such as a clinician or a physician's assistant. Specifically, the present disclosure is directed to devices and methods for vision screening where the patient is located at various distances from the vision screening device, based on specific requirements of the vision screening test(s). An example vision screening device of the present disclosure may be portable and/or hand-held, and include an oversampling sensor to capture one or more images and/or video of an environment in which the patient is located, such as an examination room. An extent of the environment captured, e.g., a field-of-view of the oversampling sensor, may be based on a maximum distance of the patient from the vision screening device, and a range of movement that may be expected to occur during the vision screening. Methods implemented by the vision screening device may determine a location of the patient's face and/or eyes in the captured image(s) using computer vision and machine learning techniques, and provide the operator with guidance to perform non-critical alignment of the vision screening device to center the eyes in the field-of-view. The vision screening device may also implement an automated mode where the operator is not required to center the eyes in the field-of-view, and instead, the device generates centered image(s) of target areas, such as the eyes, of the patient by automatically identifying a relevant portion of the oversampling sensor and extracting corresponding image data from the relevant portion. A field-of-view and resolution of the oversampling sensor may be selected so that the extracted image data of the target areas, such as the eyes, have sufficient resolution for subsequent analysis related to the vision screening test(s).

In an example vision screening device of the present disclosure, image processing and computer vision techniques implemented by the vision screening device may track the eye(s) of the patient continuously, or intermittently at pre-set intervals, in real-time or near real-time. The vision screening device may use output of the tracking to update the locations of the eye(s), and use the updated locations to generate stabilized eye image(s), where the locations of the eyes within the eye image(s) remain substantially fixed. Tracking and localization of the eye(s) may compensate for effects of small movements, including movement of the device or of the patient's head, and enable the vision screening device to provide real-time image stabilization over the duration of the vision screening.

In some example environments, the patient may be illuminated by ambient light during localization of the eyes. Subsequent to achieving desired locations of the eyes in the field-of-view, radiation of different wavelength bands of electromagnetic spectrum (e.g., infrared, near-infrared, and visible light) may be used to illuminate the eyes and/or internal structures of the eyes, as required by the vision screening test(s) being administered, and image(s) of the eyes may be generated under different illumination conditions. The vision screening device may determine, based on analysis of the captured images, one or more diseases and/or deficiencies of the eyes, such as myopia, hypermetropia, cataracts, tumors, ametropia, retinal detachment or lesions, color vision deficiencies and the like, associated with one or both eyes of the patient.

As will be described with respect to at least FIG. 1, an example vision screening device associated with screening for diseases and deficiencies of the eyes may include components for capturing images of the eye(s) of the patient under visible light illumination, as well as under illumination by radiation in the near-infrared and other bands of electromagnetic spectrum. The device may include components for capturing image(s) under ambient light using an oversampling sensor of a camera, and analyzing the captured oversampled image(s) to extract a portion of image data corresponding to image(s) of the patient's eye(s) (e.g., eye image(s)). The device may further include components for analyzing the resulting eye image(s) to determine whether the eye image(s) meets certain criteria. In examples, these criteria may include determining whether the eye image(s) have an acceptable resolution and sharpness, and whether size and positions of the eyes in the eye image(s) are within acceptable ranges. The device may also include components for tracking the eye(s) and maintaining a bounding box around the eyes (e.g., eye bounding box) within boundaries of the oversampled image, indicating an area of the oversampled image corresponding to the eye image. The image data within the eye bounding box may be extracted from the oversampled image to generate the eye image. In addition, the vision screening device may include components for performing vision screening test(s), analyzing the eye image (s) to determine disease conditions and/or deficiencies in the eye(s) of the patient, and components for determining and reporting of output(s) indicating the disease conditions and/or deficiencies detected during the vision screening.

Additional details pertaining to the above-mentioned devices and techniques are described below with reference to FIGS. 1, 2A-C, 3A-B, and 4. It is to be appreciated that while these figures describe devices and systems that may utilize the claimed methods, the methods, processes, functions, operations, and/or techniques described herein may apply equally to other devices, systems, and the like.

FIG. 1 illustrates an example environment 100 for administering vision screening tests, and in particular, screening tests for detection of diseases and/or deficiencies of eye(s) that require a patient to be located at various distances from a vision screening device, according to some implementations. As illustrated in FIG. 1, in some examples an operator 102 may administer vision screening tests, via a vision screening device 104, on a patient 106 to determine eye health of the patient 106. As described herein, the vision screening device 104 may perform one or more vision screening tests, including screening for diseases and/or deficiencies of eye(s). For example, the vision screening device 104 may be configured to perform vision screening tests such as a visual acuity test, a refractive error test, an accommodation test, dynamic eye tracking tests, color vision screening test and/or any other vision screening tests, and results of such tests may be used for assessing vision health or diagnosing ocular conditions of the patient 106.

In examples, the vision screening device 104 may comprise a portable device configured to perform the one or more vision screening tests. In some examples, the vision screening device 104 may be a handheld device, such as a mobile device similar to a tablet or a smartphone. Due to its portable nature, the vision screening device 104 may perform the vision screening tests at any location, from conventional screening environments, such as schools and medical clinics, to physician's offices, hospitals, eye care facilities, various group settings outside a medical office, and/or other remote and/or mobile locations. It is also envisioned that the vision screening device 104 may be used for administering vision screening tests to all age groups, including newborns and young children and geriatric patients.

As described herein, the vision screening device 104 may be configured to perform one or more vision screening tests on the patient 106. The vision screening test(s) performed using the vision screening device 104 may have respective recommended distance requirements, indicating a distance or a distance range to be maintained between the vision screening device 104 and the patient 106 during the administration of the test, that must be met in order to ensure accurate testing results. For instance, during a refractive error test performed using the vision screening device 104, it may be recommended that the patient 106 be spaced from the vision screening device 104 by a distance of approximately three feet or approximately one meter. In other examples, the recommended distances for administering specific vision screening tests may be six, twelve, or up to twenty-two feet between the vision screening device 104 and the patient 106. In examples of the present disclosure, the vision screening device 104 may be configured to operate at various distances from the patient 106, and generate stabilized image(s) of the eye(s) of the patient 106, compensating for small relative movements between the vision screening device 104 and the patient 106. The vision screening device 104 may automatically acquire eye image (s), and maintain the eye(s) at specific position(s) within the eye image(s), while operating at different distances from the patient 106. Alternatively, or in addition, the vision screening device 104 may provide instructions to the operator 102 and/or the patient 106 to adjust positioning of the patient 106 and/or the vision screening device 104 to achieve proper positioning of the eye(s), as required for the vision screening test(s) being administered.

To enable the features described above, the vision screening device 104 may include a camera 108 equipped with an oversampling sensor 110, as shown schematically in FIG. 1. The oversampling sensor 110 of the camera 108 may be configured to capture, under ambient lighting conditions, reflected light from an environment in which the patient 106 is located. The oversampling sensor 110 of the camera 108 may have an extended field-of-view that includes an area of the environment around the patient 106, so that the patient 106 may be detectable within the field-of-view of the oversampling sensor 110 even when the patient 106 is not centrally positioned in the field-of-view of the camera 108 of the vision screening device 104. A resolution of the oversampling sensor 110 may be selected so that image data of the target areas of the patient 106, such as the eyes, have sufficient resolution for subsequent analysis related to the vision screening test(s) even when the patient 106 is located at a maximum distance of operation supported by the vision screening device 104. The oversampling sensor 110 and methods associated with extraction of the target areas (e.g., corresponding to the eyes) of the oversampled image(s) and/or video are described in further detail with reference to FIGS. 2A-2C.

The camera 108 may also include optics components (not shown) that include one or more lenses, windows, prisms, filters, mirrors, and/or any other devices configured to collect and direct a reflected beam from the patient 106 to the oversampling sensor 110. In some examples, the camera 108 may be equipped with lenses providing a wide-angle image capture capability. For example, the camera 108 operating in a wide-angle capture mode may enable the vision screening device 104 to locate the patient 106 in an examination room. The camera 108 may also capture video of the patient while the vision screening tests are being administered. The camera 108 may generate oversampled images and/or video of the environment, which may be processed to generate image data corresponding to target areas, such as the eye(s) of the patient 106. The oversampled images and/or video may be stored in various formats, such as JPEG, BITMAP, TIFF, etc. (for images) and MP4, MOV, WMV, AVI etc. (for video).

Further steps associated with administering one or more vision screening tests may be performed while the spacing and alignment of the target areas are achieved and/or maintained using methods associated with the camera 108 and the oversampling sensor 110. In examples, the one or more vision screening tests may include illuminating the eye(s) of the patient 106 with radiation in one or more bands of the electromagnetic spectrum, and capturing images of reflected radiation from the eye(s) or parts of the eye(s) of the patient 106. For example, a refractive error screening test is based on pupil images captured under different illumination patterns generated by near-infrared (NIR) radiation sources. In other examples, vision screening tests, such as a red reflex test, may include illuminating the eye(s) of the patient 106 with visible light, and capturing image(s) of the eye(s) under visible light illumination. The vision screening device 104 may acquire data comprising images and/or video data of the eye(s) under various illumination, and detect pupils, retinas, and/or lenses of the eye(s) of the patient 106. These data may be used to assist the operator 102 or a clinician in diagnosing diseases and deficiencies of the eye(s) of the patient 106. The vision screening device 104 may also be configured to process the image(s) and/or video data to screen for diseases and deficiencies of the eye(s) such as ametropia, strabismus, and retinal conditions. As such, additional components of the vision screening device 104 described herein may also provide an automated diagnosis and/or recommendation based on the analysis of the images captured by the vision screening device 104.

The vision screening device 104 may include one or more radiation source(s) 112 configured to perform functions associated with administering one or more vision screening tests. The radiation source(s) 112 may comprise individual radiation emitters, such as light-emitting diodes (LEDs), which may be arranged in a pattern to form an LED array. In examples, the radiation source(s) 112 may include infrared or near-infrared (NIR) radiation emitters, such as NIR LEDs, which may provide coherent and collimated illumination for measuring the refractive error of the eye(s) of the patient 106 using photorefraction methods. The NIR radiation emitters of the radiation source(s) 112 may also be used for measuring the gaze angle or gaze direction of the eye(s) of the patient 106. In addition, the radiation source(s) 112 may also include visible light and color LEDs for generating color and white light stimuli for display to the patient 106 during various vision screening tests.

The vision screening device 104 may also include one or more radiation sensor(s) 114, such as infrared cameras, configured to capture reflected radiation from the eye(s) of the patient during the vision screening test(s). For example, the vision screening device 104 may emit, via the radiation source(s) 112, one or more beams of radiation, and may be configured to direct such beams at the eye(s) of the patient 106. The vision screening device 104 may then capture, via the radiation sensor(s) 114, corresponding radiation that is reflected back (e.g., from pupils of the eye(s)). In examples, the radiation sensor(s) 114 may comprise NIR radiation sensor(s) to capture reflected NIR radiation while the eye(s) of the patient 106 are illuminated by the NIR radiation source(s) 112. The data captured by the NIR radiation sensor(s) 114 may be used in the measurement of the refractive error and/or gaze angle(s) of the eye(s) of the patient 106.

The vision screening device 104 may transmit the data captured by the radiation sensor(s) 114, the oversampled image data captured by the oversampling sensor 110, and/or the image data corresponding to the target areas (e.g., the eye images), via a network 116, to a vision screening system 118 for analysis to determine an output 120 associated with the patient 106. The transmitted data may include images and/or video illustrating the pupils, retinas, and/or lenses of the eyes of the patient 106. The data may be transmitted intermittently, during specific periods of the vision screening test(s), or during the entire duration of the test(s). In some examples, the vision screening device 104 may perform the extraction of the image data corresponding to the target areas locally, and transmit only the extracted image data to the vision screening system 118 for further analysis. Alternatively, or in addition, the vision screening device 104 may perform some or all of the analysis locally to determine the output 120. Indeed, in any of the examples described herein, some or all of the disclosed methods may be performed in whole or in part by the vision screening device 104 independently (e.g., without the vision screening system 118 or its components), or by the vision screening system 118 independently (e.g., without the vision screening device 104 or its components). For instance, in some examples, the vision screening device 104 may be configured to perform any of the vision screening tests, and/or other methods described herein without being connected to, or otherwise in communication with, the vision screening system 118 via the network 116. In other example, the vision screening system 118 may include one or more components that are similar to and/or the same as those included in the vision screening device 104, and thus, the vision screening system 118 may be configured to perform any of the vision screening tests, and/or other methods described herein without being connected to, or otherwise in communication with, the vision screening device 104.

The vision screening device 104 may also include one or more display screen(s), such as display screen 122 and display screen 124, which may be color LCD (liquid crystal display), or OLED (organic light-emitting diode) display screens. The display screen 122 may be an operator display screen facing a direction towards the operator 102, configured to provide information related to the vision screening tests to the operator 102. The information may include guidance for positioning and alignment of the patient 106 with respect to vision screening device 104. The vision screening device 104 may also display the eye image(s) generated by the device 104 on the display screen 122. The eye image(s) may be displayed in real-time or near real-time during the vision screening process. In any of the examples described herein, the display screen 122 facing the operator 102 may be configured to display and/or otherwise provide the output 120 generated by the vision screening device 104 and/or generated by the vision screening system 118. The output 120 may include testing parameters, current status and progress of the screening test(s), measurements(s) determined during the test(s), image(s) captured or generated during the screening test(s), a diagnosis determined based on one or more tests, and/or a recommendation associated with the diagnosis. The display screen 122 facing the operator 102 may also display information related to or unique to the patient, and the patient's medical history.

In some examples, the vision screening device 104 may also include a display screen 124 facing in a direction towards the patient 106, and configured to display content to the patient 106. The content may include attention-attracting images and/or video to attract attention of the patient and hold the patient's gaze towards the vision screening device 104. Content corresponding to various vision screening test(s) may also be presented to the patient 106 on the display screen 124. For example, the display screen 124 may display color stimuli to the patient 106 during a color vision screening test, or a Snellen eye chart during a visual acuity screening test. The display screens 122, 124 may be integrated with the vision screening device 104, or may be external to the device, and under computer program control of the device 104. The vision screening device 104 may correspond to example vision screening device configurations described in U.S. patent application Ser. No. 17/886,920, filed on Aug. 12, 2022, the entire disclosure of which is incorporated herein by reference.

The vision screening device 104 may transmit the data captured by the camera 108 and/or the radiation sensor(s) 114, via the network 116, using network interface(s) 126 of the vision screening device 104. In addition, the vision screening device 104 may also similarly transmit other testing data associated with the vision screening test(s) being administered, (e.g., type of test, duration of test, patient identification and the like). The network interface(s) 126 of the vision screening device 104 may be operably connected to one or more processor(s) 128 of the vision screening device 104, and may enable wired and/or wireless communications between the vision screening device 104 and one or more components of the vision screening system 118, as well as with one or more other remote systems and/or other networked devices. For instance, the network interface(s) 126 may include a personal area network component to enable communications over one or more short-range wireless communication channels, and/or a wide area network component to enable communication over a wide area network. In any of the examples described herein, the network interface(s) 126 may enable communication between, for example, the processor(s) 128 of the vision screening device 104, and the vision screening system 118, via the network 116. The network 116 shown in FIG. 1 may be any type of wireless network or other communication network known in the art. Examples of network 116 include the Internet, an intranet, a wide area network (WAN), a local area network (LAN), and a virtual private network (VPN), cellular network connections and connections made using protocols such as 802.11a, b, g, n and/or ac.

As described herein, a processor, such as the processor(s) 128, can be a single processing unit or a number of processing units, and can include single or multiple computing units or multiple processing cores. The processor(s) 128 can be implemented as one or more microprocessors, microcomputers, microcontrollers, digital signal processors, central processing units, state machines, logic circuitries, and/or any devices that manipulate signals based on operational instructions. For example, the processor(s) 128 can be one or more hardware processors and/or logic circuits of any suitable type specifically programmed or configured to execute the algorithms and processes described herein. As shown schematically in FIG. 1, the vision screening device 104 may also include computer-readable media 130 operably connected to the processor(s) 128. The processor(s) 128 can be configured to fetch and execute computer-readable instructions stored in the computer-readable media 130, which can program the processor(s) 128 to perform the functions described herein.

The computer-readable media 130 may include volatile and nonvolatile memory and/or removable and non-removable media implemented in any type of technology for storage of information, such as computer-readable instructions, data structures, program modules, or other data. Such computer-readable media 130 can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. The computer-readable media 130 can be a type of computer-readable storage media and/or can be a tangible non-transitory media to the extent that when mentioned, non-transitory computer-readable media exclude media such as energy, carrier signals, electromagnetic waves, and signals per se.

The computer-readable media 130 can be used to store any number of functional components that are executable by the processor(s) 128. In examples, these functional components comprise instructions or programs that are executable by the processor(s) 128 and that, when executed, specifically configure the one or more processor(s) 128 to perform actions associated with one or more of the vision screening tests used for the detection and diagnosis of diseases and deficiencies of the eye(s). For example, the computer-readable media 130 may store one or more functional components for administering vision screening tests, and for positioning and alignment of the eye(s) during the administration of the vision screening tests. For example, the components may include an image capture and analysis component 132, an eye image validation component 134, an eye tracking and output generation component 136 and/or a patient screening component 138, as illustrated in FIG. 1. At least some of the functional components of the vision screening device 104 will be described in detail below.

In examples, the image capture control component 132 may be configured to operate the camera 108 of the vision screening device 104 to capture oversampled image(s) of the patient 106 and surrounding environment, and identify a portion of the oversampled image(s) corresponding to the eye(s) of the patient 106. In some examples, the image capture control component 132 may analyze the image and/or video data captured by the oversampling sensor 110 (e.g., the oversampled image) to determine an area of the image data corresponding to the patient's 106 face (e.g., face image). Algorithms for detecting human faces in digital images/video are well known in the art of digital image processing, and typically generate an output indicating a bounding box surrounding each detected face and/or location(s) of the eye(s) in the face. The image capture control component 132 may implement a face detection algorithm to detect the bounding box corresponding to the patient's 106 face, and determine an area of the oversampled image corresponding to the face that includes the area within the bounding box. The image capture control component 132 may further process the area corresponding to the face to determine locations of the eyes of the patient 106. Algorithms for determining locations of facial features, such as eyes, mouth etc., within a face area in a digital image are well known in the art e.g., active appearance models and active shape models of the human face, and other geometric or appearance-based models of eye and/or pupils of the eyes.

Alternatively, or in addition, the image capture control component 132 may determine locations of the eyes of the patient 106 by implementing an eye detection algorithm. Machine learning algorithms trained to detect eyes in images are known in the art, and may be based on convolutional neural networks (CNNs) or traditional object classifiers. Some face detection algorithms may also generate eye locations as part of the output. The eye detection algorithm may output a bounding box around the eyes, determine location of center(s) of the eye(s), locations of inner and outer corners of the eye(s), and/or location of features of the eye(s), such as pupils of the eye(s). Eye detection algorithms known in the art also work in a similar manner on infrared and near-infrared (NIR) images. In some examples, the image capture control component 132 may apply an eye detection algorithm on NIR image(s) captured by the radiation sensor(s) 114 to determine the eye locations.

Alternatively, or in addition, the image capture control component 132 may determine locations of the eyes from infrared image(s) captured by the radiation sensor(s) 114 while the eyes of the patient 106 are illuminated by the infrared radiation emitted by emitters of the radiation source(s) 112. Reflection of infrared radiation from irises of the eyes of the patient 106 makes the pupils of the eyes of the patient 106 appear as nearly circular spots of high brightness or intensity in the captured infrared image(s). The image capture control component 132 may implement image processing techniques to determine high intensity areas in the infrared image(s) that may be candidate areas for being the pupils of the eyes of the patient 106. The image capture control component 132 may determine the candidate areas based on criteria including a high average intensity value, a nearly circular shape, and/or a diameter of the area matching an expected diameter of the pupils of the eyes of the patient 106 based on the distance of the patient 106 from the vision screening device 104. The image capture control component 132 may determine a score for each candidate area based on the criteria. Additional weight may be assigned to candidate areas where a first candidate area can be associated with a second candidate area at a distance matching an expected distance between the pupils of the eyes of the patient 106 based on the distance of the patient 106 from the vision screening device 104. In some examples, the image capture control component 132 may determine the highest scoring candidate area or a pair of candidate areas as the locations of the pupils of the eyes of the patient 106.

In other examples, the operator 102 may provide an initial location(s) of the eye(s) of the patient 106. For example, the oversampled image may be displayed to the operator 102 on the display screen 122, and a user interface of the vision screening device 104 may enable the operator 102 to click on or otherwise indicate locations of the center(s) of the eye(s) in the displayed image.

Based on determining the locations of the eyes(s) using one or more of the methods described above, the image capture control component 132 may determine an eye bounding box indicating an area of the oversampled image corresponding to the eyes of the patient 106. In addition, in some examples, the image capture control component 132 may extract image data corresponding to the area within the eye bounding box to generate an eye image of the patient 106. In other examples, the image capture control component 132 may specify the eye bounding box and provide the associated oversampled image, without extracting the eye image.

In some examples, the camera 108 may be equipped with auto-focus zoom lens(es) that can provide telephoto as well as wide-angle image capture capability. In such examples, the image capture control component 132 may operate the camera 108 in a telephoto zoom mode to capture a zoomed-in image of the patient's eyes based on the determined location of the eye bounding box. In other examples, the image capture control component 132 may apply the face detection algorithm(s) to determine a face area, capture a zoomed-in image of the face area, and apply the eye detection algorithms to the zoom-in image to determine the eye bounding box.

The image capture control component 132 may specify the eye bounding box identifying a portion of the over-sampled image corresponding to one or more eye(s) of the patient 106, using (x,y)-coordinates of corners of the eye bounding box relative to an origin (0, 0) of the oversampled image. In some examples, the image capture control component 132 may generate the eye bounding box in real-time or near real-time by processing oversampled images captured and processed at frequent periodic intervals (e.g., at rates of 2 images per second, 10 images per second, or higher), or by processing oversampled images corresponding to frames of the video captured by the camera 108. Further, in some examples, the image capture control component 132 may update the eye image in real-time or near real-time by extracting image data from the oversampled image, corresponding to data within the eye bounding box(es). One or more of the eye image(s) may be included in the output 120. The functions and features of the image capture and analysis component 132 will be described in further detail with reference to FIGS. 2B, 2C and 3A.

In examples, computer-readable media 130 may additionally store the eye image validation component 134 configured to determine whether the eye image(s), as generated by the image capture and analysis component 132, or as indicated by the eye bounding box determined by the image capture and analysis component 132, meet requirements specified in pre-determined validity criteria. The validity criteria may be based on requirements of the vision screening test(s) being administered. For example, the eye image(s) may be required to have a minimum pixel resolution and sharpness level so that features of the eye(s) used to determine diseases and/or deficiencies of the eyes are detectable. In addition, location of pupils of the eyes may be required to be centered in the eye images and/or horizontally aligned. For example, spacing between the location of pupil of the first eye and the pupil of the second eye may be reduced due to out-of-plane rotation of the patient's head relative to the vision screening device 104, where the reduction of spacing is proportional to the degree of out-of-plane rotation. In another example, the pupils may not be aligned horizontally due to in-plane rotation of the patient's head. The validity criteria may be related to maximum allowable amounts of in-plane and out-of-plane rotations that may be exhibited in the eye image(s) without affecting requirements of the vision screening test(s). Methods associated with the eye image validation component 134 will be described in further detail with reference to FIG. 3B.

In addition, the eye image validation component 134 may determine a distance of the patient 106 relative to the vision screening device 104 e.g., based on an output of a range sensor associated with the vision screening device 104 and/or based on size of the eyes or spacing between center(s) of the eyes. For example, the vision screening device 104 may be equipped with a range finder, such as an ultra-sonic range finder, an infrared range finder, and/or any other proximity sensor that may be able to determine the distance of the patient 106 from the screening device. In examples, each vision screening test may have a recommended distance between the vision screening device 104 and the patient 106 and/or a recommended position of the patient 106 relative to the vision screening device 104.

In the instance that the patient's distance and/or position of the eye(s) do not satisfy the recommendation of the vision screening test being administered, the eye image validation component 134 may provide instructions to the operator 102, via the display screen 122, indicating that the patient 106 and/or the vision screening device 104 needs to be moved, along with adjustments required to bring the patient into a correct position for administering the vision screening test. The eye image validation component 134 may determine whether the eye image(s) meet the validity criteria.

In examples, the vision screening device 104 may re-run the steps associated with the image capture and analysis component 132 after the operator 102 re-positions the patient 106 and/or the vision screening device 104 according to the adjustments suggested.

In some examples, the vision screening device 104 may implement the eye tracking and output generation component 136 configured to use eye tracking algorithms known in the art on a video feed of the patient or images captured at pre-set intervals (e.g., using video and images captured by the camera 108), to produce a focused and centered image of the eye(s). The eye tracking and output generation component 136 may initialize the eye tracking algorithm (e.g., deep learning-based or Kalman filtering-based eye trackers)

by using eye locations generated by the image capture and analysis component 132, and subsequently determine a current eye location in real-time or near real-time in response to small movements of the patient 106 or the vision screening device 104. The eye tracking algorithm may output locations of pupils and/or other features of the eyes, and/or a center of nose bridge. The eye tracking and output generation component 136 may continuously or intermittently (e.g., at pre-set intervals) update an initial position of the eye bounding box generated by the image capture and analysis component 132 based on the locations of the eyes output by the eye tracking algorithm. In some examples, a size and dimensions of the eye bounding box may not change, and the eye tracking and output generation component 136 may only update location of a specific corner (e.g., top left corner) of the eye bounding box to specify a new location. Further, the eye tracking and output generation component 136 may extract image data, from the oversampled image, corresponding to the eye bounding box to generate stabilized eye image(s), which may be presented to the operator 102 on the display screen 122 and/or processed further to determine the output 120 associated with the patient 106. One or more of the stabilized eye image(s) may be included in the output 120. The functions and features of the eye tracking and output generation component 136 will be described in further detail with reference to FIG. 2C.

In examples, the image capture control component 132 may transmit the oversampled image to the vision screening system 118, and subsequently, the eye tracking and output generation component 136 may transmit a sequence of (x,y) coordinates of a specific corner (e.g. top-left) of the eye bounding boxes over time, continuously updating the current location of the eye bounding box. The vision screening system 118 may extract and process a current eye image from the oversampled image based on the current location of the eye bounding box. In other examples, other components of the vision screening device 104 may receive the oversampled image and the sequence of eye bounding box locations for further processing.

In examples, computer-readable media 130 may additionally store the patient screening component 138 which may be configured to store and/or access patient data 140 associated with the patient 106. For example, the patient data 140 may include demographic information such as name, age, ethnicity, and the like. When the vision screening device 104 and/or vision screening system 118 initiates a vision screening test, the patient 106 may provide, or the operator 102 may request, from the patient 106 or a guardian of the patient 106 the patient data 140 regarding the patient's demographic information, medical information, preferences, and the like. In such examples, the operator 102 may request the data while the screening is in progress, or before the screening has begun. In some examples, the operator 102 may be provided with predetermined categories associated with the patient 106, such as predetermined age ranges (e.g., newborn to six months, six to twelve months, one to five years old, etc.), and may request the patient data 140 in order to select the appropriate category associated with the patient 106. In other examples, the operator 102 may be provided a free form input associated with the patient data 140. In still further examples, an input element may be provided to the patient 106 directly.

Alternatively, or in addition, the patient screening component 132 may be configured to receive, access, and/or store the patient data 140 associated with the patient 106 and/or additional patients. For example, the patient screening component 132 may store previous patient information associated with the patient 106 and/or other patients. For instance, the patient screening component 132 may store previous screening history of the patient 106, including data from previous screening such as color images, NIR images, and/or video of the eye(s) of the patient 106. The patient screening component 132 may receive the patient data 140 and/or may access such information via the network 116. For example, the patient screening component 132 may access an external database, such as screening database 144, storing data associated with the patient 106 and/or other patients. The screening database 144 may be configured to store the patient data 140 in association with a patient ID. When the operator 102 and/or the patient 106 enters the patient ID, the patient screening component 132 may access or receive the patient data 140 stored in association with the patient ID of the patient 106.

In examples, the patient screening component 138 may be configured to determine the vision screening test(s) to administer to the patient 106 based at least in part on the patient data 140. For example, the patient screening component 138 may utilize the patient data 140 to determine a testing category that the patient 106 belongs to (e.g., a testing category based on age, medical history, etc.). The patient screening component 138 may determine the vision screening test(s) to administer based on the testing category. For example, if the patient data 140 indicates that the patient is a newborn, the selected vision screening test(s) may include screening for congenital conditions of the eye such as congenital cataracts, retinoblastoma, opacities of the cornea, strabismus and the like. In addition, eye abnormalities may be associated with systemic inherited diseases such as Marfan syndrome and Tay-Sachs disease. For example, a screening test for a characteristic red spot in the eye may indicate Tay-Sachs disease. As another example, if the patient data 140 indicates that the patient is above fifty years old, the patient screening component 138 may determine that the vision screening test(s) include screening for onset of cataracts, macular degeneration and other age-related eye diseases.

The patient screening component 138 may also determine vision screening test(s) based on the patient's medical history. For example, the screening database 144 may store, in the patient data 140, medical history associated with previous vision screening tests of the patient 106, including test results, images of the eye(s), measurements, recommendations, and the like. The patient screening component 138 may access the patient data 140 including medical history from the screening database 144 and determine vision screening test(s) to administer to monitor status and changes in previously detected vision health issues. For example, if a progressive eye disease, such as onset of cataracts or macular degeneration, was detected in a previous screening, further screening may be administered to track the development of the disease. As another example, if the patient 106 had surgery for removal of a tumor of the eye(s), the vision screening test(s) may include screening for further tumors or scarring in the eye(s).

Further, the patient screening component 138 may be configured to receive, access, and/or analyze data from other components of the vision screening device 104, and may store the output 120, which may include a recommendation, diagnosis, measurements, captured images/video and/or the generated eye images in a database, such as the screening database 144, for evaluation by a clinician, or for access during subsequent vision screening(s) of the patient 106. The screening database 144 may provide access to authorized medical professionals to enable printing of reports or further assessment of the data related to the screening of the patient 106.

Although FIG. 1 illustrates example processor(s) 128 and computer-readable media 130 storing an image capture and analysis component 132, an eye image validation component 134, an eye tracking and output generation component 136, a patient screening component 138 and/or other components of the vision screening device 104, in any of the examples described herein, the vision screening system 118 may include similar components and/or the same components. In such examples, the vision screening system 118 may include processor(s) 146 and computer-readable memory 148 that are configured to perform the functions of some or all of the components in the computer-readable memory 130 of the vision screening device 104. For example, one or more of the components of the computer-readable memory 130 may be included in analysis component(s) 150 of computer-readable memory 148 and be executable by the processor(s) 146. In such examples, the vision screening system 118 may communicate with the vision screening device 104 using network interface(s) 152, and via the network 116, to receive data from the vision screening device 104 and send results (e.g., output 120), back to the vision screening device 104. The vision screening system 118 may be implemented on a computer proximate the vision screening device 104, or may be at a remote location. For example, the vision screening system 118 may be implemented as a cloud service on a remote cloud server.

The vision screening system 118 may be configured to receive data, from the vision screening device 104 and via the network 116, collected during the administration of the vision screening test(s). In some examples, the image capture and analysis component 132 or the eye tracking and output generation component 136 may send the oversampled image, via the network 116, to the vision screening system 118, and subsequently send information specifying the eye bounding box(es) and updates to the eye bounding box(es) to be applied to the oversampled image to extract the eye image(s). In some examples, based at least in part on processing the data corresponding to the eye images, the vision screening system 118 may determine the output 120 associated with the patient 106. For example, the output 120 may include a recommendation and/or diagnosis associated with eye health of the patient 106, based on an analysis of the eye images(s) and/or NIR image data indicative of diseases and/or deficiencies associated with the eye(s) of the patient 106. The vision screening system 118 may communicate the output 120 to the processor(s) 128 of the vision screening device 104 via the network 116. As noted above, in any of the examples described herein one or more such recommendations, diagnoses, or other outputs may be generated, alternatively or additionally, by the vision screening device 104.

The network interface(s) 152 may enable wired and/or wireless communications between the components and/or devices shown in system 100 and/or with one or more other remote systems, as well as other networked devices. For instance, at least some of the network interface(s) 152 may include a personal area network component to enable communications over one or more short-range wireless communication channels. Furthermore, at least some of the network interface(s) 152 may include a wide area network component to enable communication over a wide area network. Such network interface(s) 152 may enable, for example, communication between the vision screening system 118 and the vision screening device 104 and/or other components of the system 100, via the network 116. For instance, the network interface(s) 152 may be configured to connect to external databases (e.g., the screening database 144) to receive, access, and/or send screening data using wireless connections. Wireless connections can include cellular network connections and connections made using protocols such as 802.11a, b, g, and/or ac. In other examples, a wireless connection can be accomplished directly between the vision screening device 104 and an external system using one or more wireless protocols, such as Bluetooth, Wi-Fi Direct, radio-frequency identification (RFID), infrared signals, and/or Zigbee. Other configurations are possible. The communication of data to an external database can enable report printing or further assessment of the patient's visual test data. For example, data collected and corresponding test results may be wirelessly transmitted and stored in a remote database accessible by authorized medical professionals.

It should be understood that, while FIG. 1 depicts the system 100 as including a single vision screening system 118, in additional examples, the system 100 may include any number of local or remote vision screening systems substantially similar to the vision screening system 118, and configured to operate independently and/or in combination, and configured to communicate via the network 116.

As discussed herein, FIG. 1 depicts an exemplary vision screening device 104 that includes components for administering vision screening tests to a patient where the patient may be located at different distances from the vision screening device 104, based on the requirements of the vision screening test(s). The vision screening device may include a camera with an oversampling sensor configured to capture an area of the environment that is larger than a target area, such as the eyes. The vision screening device 104 may include one or more components for extracting an image of the target area from image data captured by the oversampling sensor, and determine that the image of the target area meets requirements of the vision screening test(s). In some examples, the one or more components may be implemented on a remote vision screening system 118 communicating with the vision screening device 104 over a network 116. The vision screening device 104 and its components are described in detail with reference to the remaining figures.

It is to be understood that though the components of the vision screening device 104, such as the image capture and analysis component 132 and the eye tracking and output generation component 136, are described in a context of vision screening, other applications of these components are also envisioned. For example, in the vision screening application described, target areas determined and tracked correspond to the eyes of the patient. In other applications, the target areas may correspond to other parts of the patient that also need to be located and extracted from the oversampled image. For example, in a skin examination if a patient, a mole or lesion on the skin may be the target area being determined and tracked. A mole or lesion may be determined based on the mole or lesion area exhibiting a different color or a different spectral response under illumination from the radiation sources of the vision screening device. The determined area may then be tracked to maintain the area in a center of the field-of-view of a screening device using techniques described above. As another example, an optic disc or a fovea may be the target area when examining a retina of the eye. The optic disc or the fovea may be determined in image(s) of the retina based on a difference in appearance between the optic disc or the fovea and a background area of the retina. The determined area may then be tracked to maintain the optic disc or the fovea in a same position in the image of the retina during the retinal examination. In yet another example, in a patient monitoring application, the components described above may be used to locate and track position of the patient in a bed, and/or track parts of the patient for monitoring bio-signs e.g., chest motion to monitor breathing. In the above examples, the methods and systems associated with a device configured for examination of target areas other than eyes may also adjust the extracted area of the oversampled image, corresponding to the target areas, to compensate for movements of the device, which may be hand-held, or the patient, who may be unrestrained, as described in the context of vision screening.

Figure 2A:
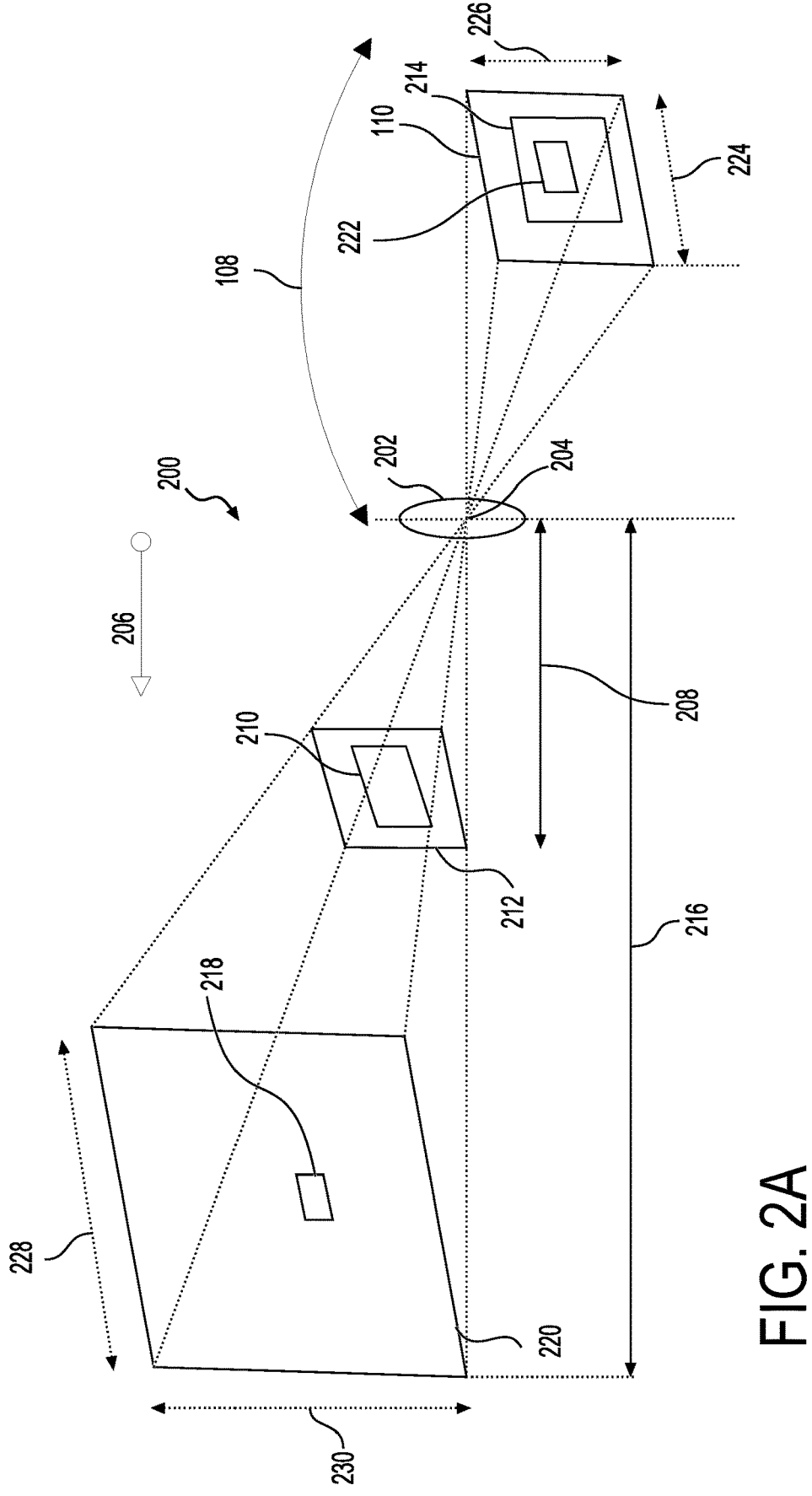
FIG. 2A illustrates an example environment of operation of a vision screening device of the present disclosure.

FIG. 2A (not drawn to scale) illustrates an example system 200 including a schematic illustration of components, such as the camera 108 equipped with the oversampling sensor 110 of the vision screening device 104 of FIG. 1, according to examples of the present disclosure. In examples, the camera 108 may also be equipped with a lens assembly 202 with an optical center at 204. The lens assembly 202 directs reflected light from an environment in front 206 of the camera 108 onto the oversampling sensor 110. The environment may be an examination room in which the patient 106 is located. During the administration of a first vision screening test, the patient 106 may be required to be located at a distance 208, which may be an approximate distance or a range of distances, from the optical center 204. The patient's eyes may be approximately located in an area 210 on a plane 212 of the environment. In this instance, reflected light from the area 210 corresponding to the eyes may be focused onto the oversampling sensor 110 by the lens assembly 202 to form an image 214.

As also shown in FIG. 2A, during the administration of a second vision screening test, the patient 106 may be required to be located at distance 216, which may be an approximate distance or a range of distances, from the optical center 204. In this instance, the patient's eyes may be approximately located in an area 218 on a plane 220 of the environment. The reflected light from the area 218 corresponding to the eyes may be focused onto the oversampling sensor 110 by the lens assembly 202 to form an image 222 on the oversampling sensor 110. In examples, the distance 208 may be the closest distance of operation of the vision screening device 104, and the distance 216 may be the farthest distance of operation of the vison screening device 104. For example, distance 208 may be approximately three feet, while distance 216 may be approximately twenty-two feet.

As illustrated in FIG. 2A, the oversampling sensor 110 of the vision screening device 104 may have a width 224 and a height 226 sufficient to support a horizontal field-of-view 228 and a vertical field-of-view 230 at the distance 216, which may be a maximum distance of operation of the vision screening device 104. In addition, the oversampling sensor 110 may have a resolution (e.g., total number of pixels obtained by multiplying the number of pixels along the width 224 and the number of pixels along the height 226)) such that the image 222 of the eyes of the patient at a maximum operating distance has sufficient resolution (e.g., number of pixels in the image 222) meeting requirements of the second vision screening test(s). As an example, if the vision screening test(s) require the eye images to be a minimum of 8 megapixels, and at the farthest distance 216, the eye image occupies 10% of the area of the oversampling sensor 110, then the resolution of the oversampling sensor 110 needs to be at least 80 megapixels, which may be satisfied by an oversampling sensor with dimensions of 10,966 pixels along the width 224 and 7,296 pixels along the height 226, as an example. It is understood that if the image 222 has sufficient resolution at the farthest distance of operation, other images of the eyes of the patient located closer to the optical center 204 would be larger, and therefore, also have sufficient resolution.

As discussed herein, FIG. 2A depicts an environment of operation of an exemplary vision screening device 104 that includes a camera 108 with an oversampling sensor 110 for administering vision screening test(s) where the patient is required to be located at different distances from the vision screening device 104. The vision screening device 104 is intended to perform an entire vision screening which may include multiple, different vision screening tests including screening for multiple diseases, deficiencies and conditions of the eyes of the patient, which may require that the patient be located at a range of distances from the device. As discussed, the vision screening device 104 is configured to capture eye images at sufficient resolution at distances between the closest and the farthest distance of operation.

Figure 2B:
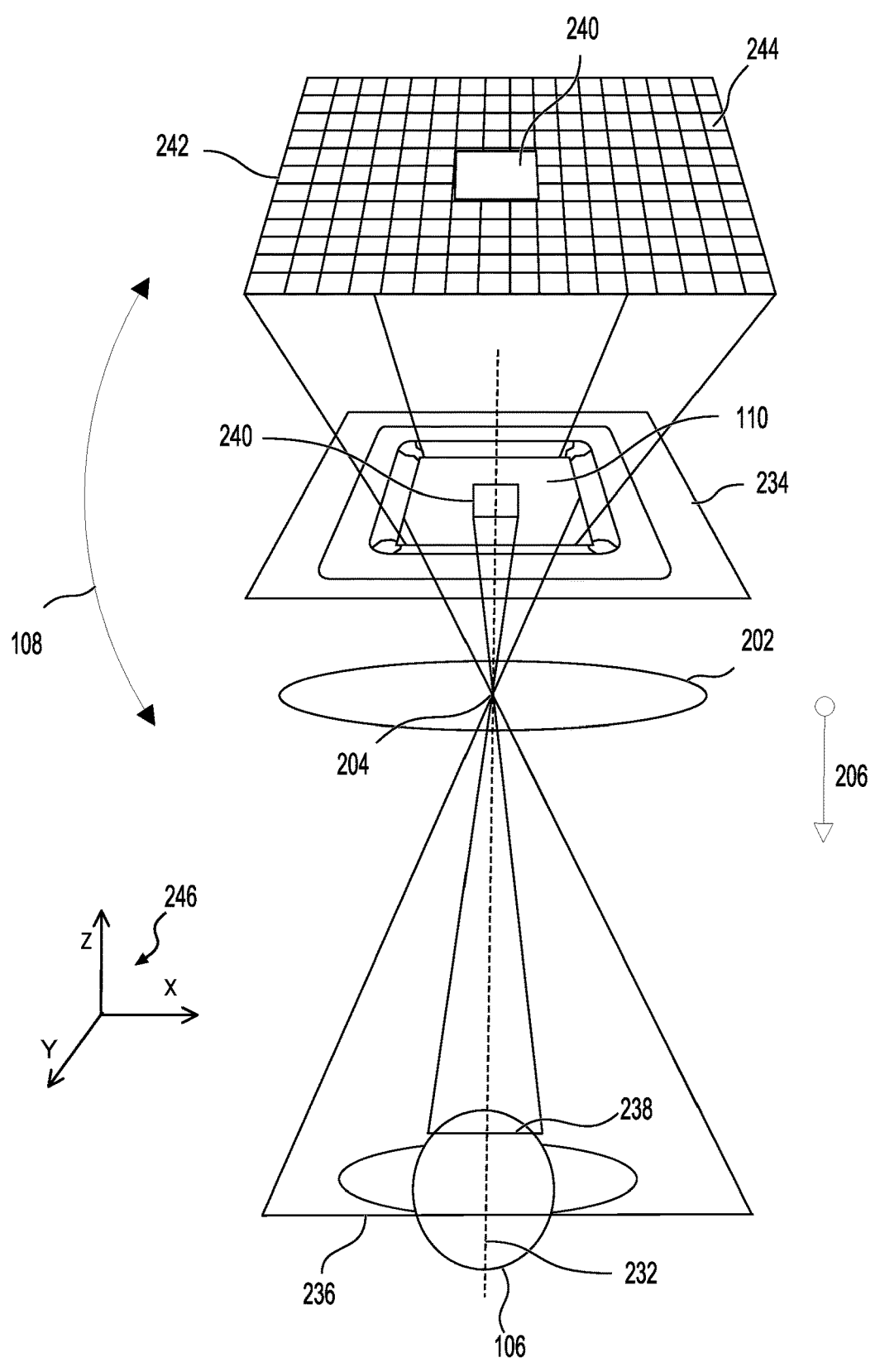
FIG. 2B provides a schematic illustration of an oversampling sensor of an example vision screening device of the present disclosure in a top view of an environment of operation of a vision screening device of the present disclosure.

FIG. 2B illustrates a top view of an environment in which a vision screening test may be administered to the patient 106, including a schematic illustration of components, such as the camera 108 equipped with the oversampling sensor 110 of the vision screening device 104 of FIG. 1. The patient 106 is positioned in front 206 of the camera 108 at a distance required by the vision screening test, and in an ideal scenario shown, the patient 106 is aligned perpendicular to an optical axis 232 of the lens assembly 202 passing through the optical center 204. As shown, the oversampling sensor 110, which may be mounted on a sensor assembly 234, captures an oversampled image 242 covering a horizontal field-of-view 236 that includes the patient 106 and a portion of the environment surrounding the patient 106. The image 242 includes an area 240 corresponding to a target area 238, such as the eyes of the patient 106 e.g., the area 240 may correspond to the eye bounding box.

As described above with reference to FIG. 1, the components of the vision screening device 104, such as the image capture and analysis component 132 and/or the eye tracking and output generation component 136, may be configured to extract image data from pixels 244 of the image 242 in the target area 240 to generate the eye image(s) of the patient 106 during the vision screening. As discussed, the vision screening device 104 may be a hand-held, portable device. Small movements of the target area 238 relative to the camera 108 is to be expected due to movements of the operator hand-holding the vision screening device, and/or movement of the head of the patient 106. As a result of the movement, a position of the area 240 corresponding to the eye bounding box may change relative to boundaries of the oversampled image 242. In addition to translational motion (e.g., where the patient is located), there may also be rotational motion of the head of the patient 106 causing changes to the position and/or orientation of the area 240. For example, a rotation of the head of the patient 106 in the X-Y plane of coordinate system 246 corresponds to an in-plane rotation with respect to the camera 108 of the vision screening device, and a rotation of the head of the patient 106 in the Y-Z plane (e.g., due to an up-and-down movement of the head) or in the X-Z plane (e.g., due to a side-to-side movement of the head) of the coordinate system 246 corresponds to an out-of-plane rotation with respect to the camera 108 of the vision screening device.

Figure 2C:
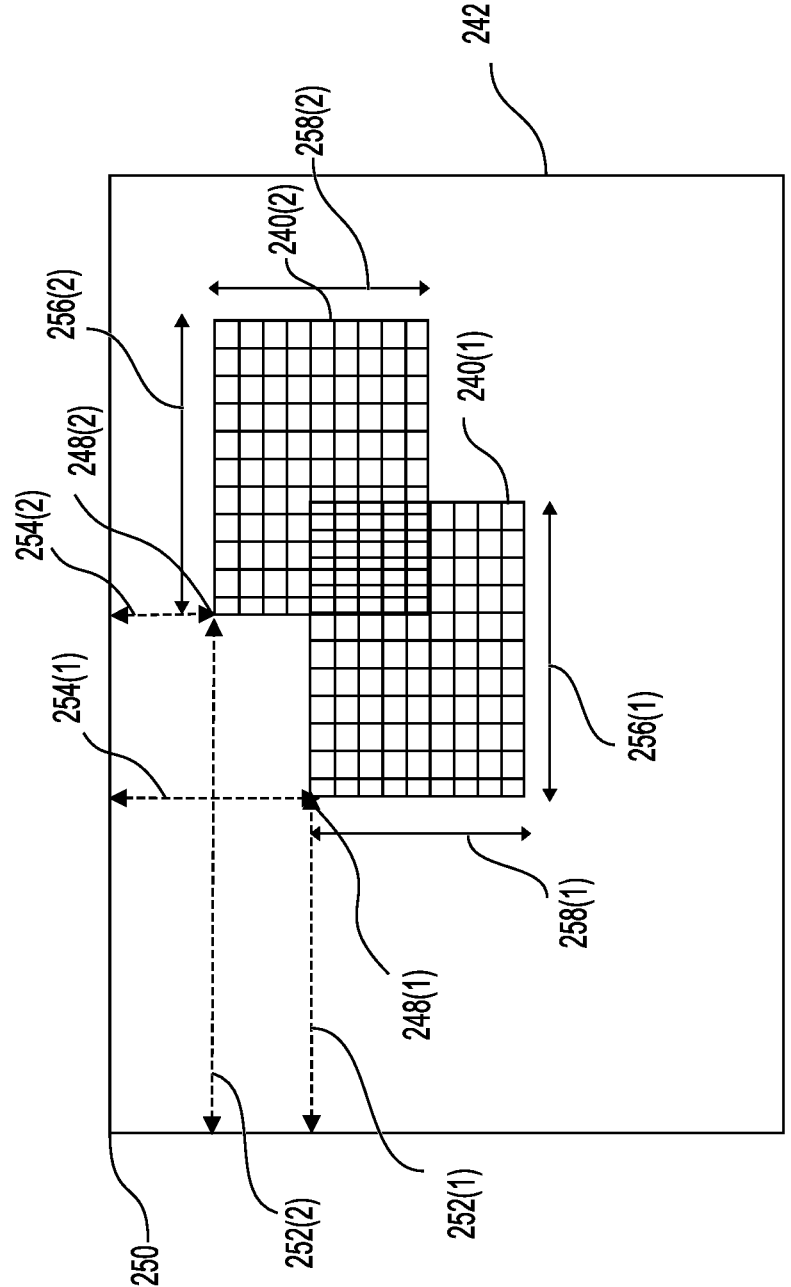
FIG. 2C provides a schematic illustration of an image captured by the oversampling sensor of FIG. 2B.

FIG. 2C illustrates tracking and extraction of the eye bounding box within the oversampled image 242. As shown, the eye bounding box 240(1) may be located at a first location at a first time, with a corner (e.g., top-left corner) 248(1) of the eye bounding box 240(1) located at coordinates $(x_1, y_1)$ with respect to an origin $(0, 0)$ 250 of the oversampled image 242, where the x-coordinate, $x_1$, corresponds to the distance 252(1) and the y-coordinate, $y_1$, corresponds to the distance 254(1). The eye bounding box 240(1) is also characterized by a width 256(1) and a height 258(1). As is known in the art, any bounding box may be uniquely characterized by a specified corner (e.g., top-left), a width and a height. The image capture and analysis component 132 or the eye tracking and output generation component 136 may represent the eye bounding box by specifying (x,y) coordinates of the top-left corner and a width and height of the eye bounding box. In other examples, the eye bounding box may be alternatively specified using two opposite corners (e.g., the top-left and the bottom-right) of the bounding box. The image capture and analysis component 132 or the eye tracking and output generation component 136 may extract image data (e.g., pixel values) from the area indicated by the eye bounding box to generate the eye image of the patient 106.

As discussed with reference to FIG. 1, the eye tracking and output generation component 136 may track the eyes of the patient, and update the location of the eye bounding box, either continuously in real-time, or intermittently at pre-defined intervals. For example, the eye tracking and output generation component 136 may determine, at a second time, the eye bounding box 240(2), which is at a second location different from the first location. The eye bounding box 240(2) may be uniquely specified by the coordinates $(x_2, y_2)$ of its top-left corner 248(2), along with width 256(2) and height 258(2). As described with respect to the eye bounding box 240(1), the x-coordinate $x_2$, corresponds to the distance 252(2) and the y-coordinate, $y_2$, corresponds to the distance 254(2). In examples, the width 256(1) may be same as the width 256(2), and the height 258(1) may be the same as height 258(2). In such examples, the eye bounding box may be specified at a second time after a first time by updating the top-left corner. In other examples, the height and width of the eye bounding box may not remain the same over time, and would need to be specified to uniquely determine location and extent of the eye bounding box.

In various examples, as described herein with reference to FIGS. 2A-2C, the vision screening device 104 may be operated at different distances from the patient 106, as required by the vision screening test(s) being administered. The vision screening device 104 may capture oversampled image(s) of the patient 106 and surrounding environment, locate the patient's face in the oversampled image, localize the eyes of the patient by specifying an eye bounding box, and generate eye images of the patient's eyes by extracting relevant image data from the oversampled image(s). In addition, the vision screening device 104 may track the eyes of the patient and compensate for small movements of the eyes relative to the vision screening device 104, by updating the eye bounding box and generating a stabilized image of the eyes of the patient 106.

Figure 3A:
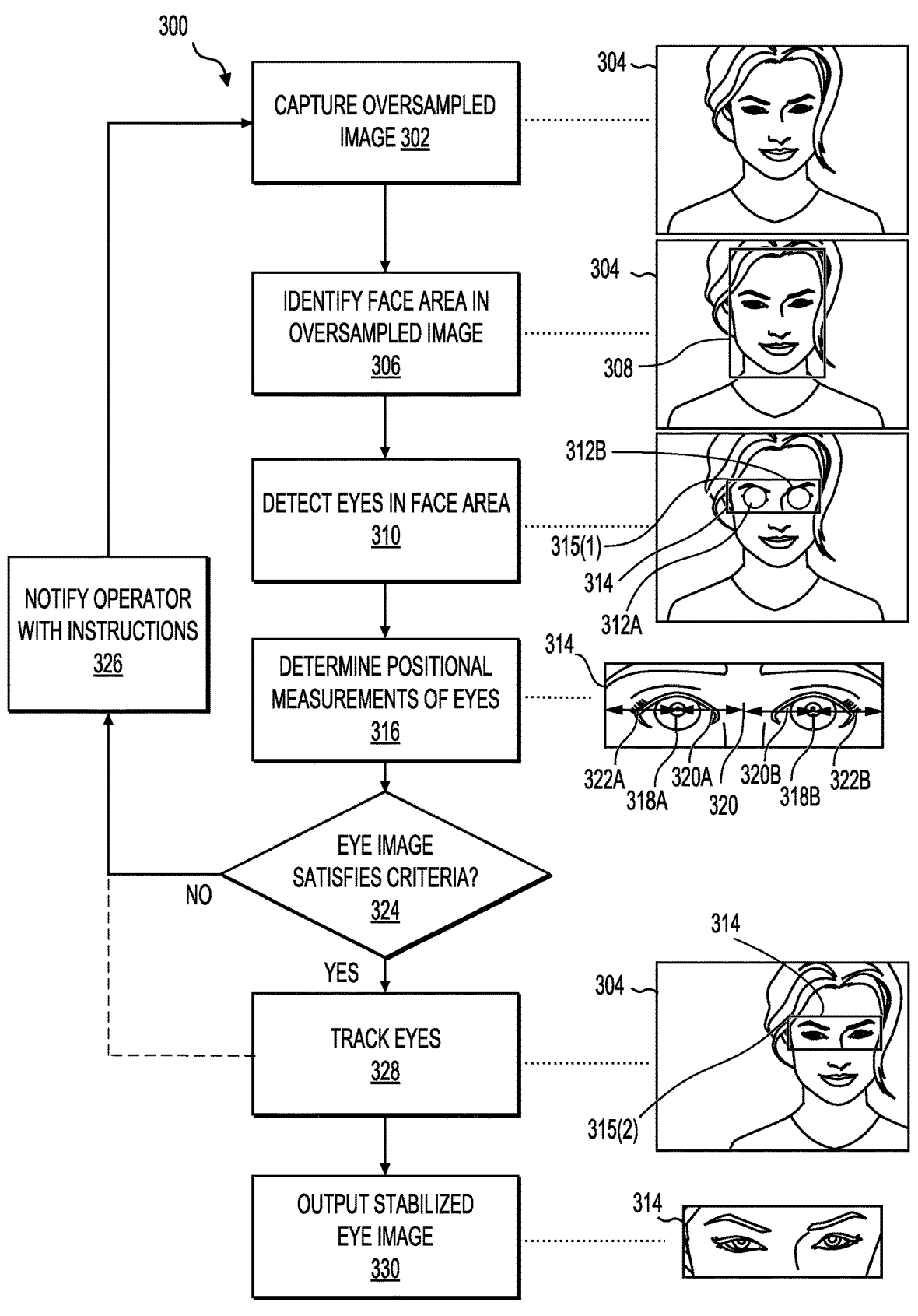
FIG. 3A provides a pictorial flow diagram of an example workflow for performing a vision screening test using the example systems and devices on the present disclosure.

FIG. 3A is a pictorial flow diagram illustrating an example workflow 300 for administering one or more of the vision screening tests above. The vision screening tests may be administered using the vision screening device 104, for example. As described with reference to FIG. 2B, the vision screening device 104 is set up so that the camera 108 of the vision screening device 104 faces a patient located in an environment in front of the vision screening device, e.g., in an examination room. In FIG. 3A, the workflow 300 is illustrated as a collection of steps or blocks in a logical flow graph, and an illustration of each step of the workflow 300 is shown associated with the step. The steps of the workflow

300 represent a sequence of operations that can be implemented in hardware, software, or a combination thereof. In the context of software, the steps represent computer-executable instructions stored on one or more computer-readable storage media that, when executed by processor(s) e.g., the processor(s) 128 or the processor(s) 146 of the vision screening system 118, perform the recited steps. The recited steps correspond to functions of one or more components described with reference to FIG. 1, such as the image capture and analysis component 132, the eye image validation component 134, and the eye tracking and output generation component 136.

In some examples, the workflow 300 may be implemented as an app running on the processor 130, and the app may provide step-by-step guidance to an operator administering the vision screening test(s) e.g., on the display screen 122 of the vision screening device 104. The guidance may include information related to correctly positioning the patient relative to the vision screening device 104, and or an indication of whether correct positioning is being maintained during the administration of the vision screening test(s).

At step 302, the processor(s) captures an oversampled image at a start of a vision screening session being administered to a patient. The vision screening device 104 may capture an oversampled image 304, which may be a captured as a part of a series of oversampled images, of the patient and surrounding environment e.g., using the camera 108 equipped with the oversampling sensor 110. In some examples, step 302 may be performed in response to an input from an operator of the vision screening device 104 selecting a vision screening test to be administered e.g., via a user interface displayed on the display screen 122. For example, vision screening tests supported by the vision screening device 104 may include photorefraction screening tests, visual acuity screening tests, dynamic eye tracking tests, accommodation tests, color vision screening tests, and the like.

At step 306, the processor(s) may identify a face area in the oversampled image 304. For example, the processor(s) may execute a face detection algorithm on the oversampled image 304 to determine a bounding box 308 corresponding to the patient's face, as described with reference to the image capture and analysis component 132 of the vision screening device 104. Some examples of face detection algorithms output a bounding box around detected face area(s). In such examples, the bounding box 308 may be the bounding box outputted by the face detection algorithm, or generated by the processor(s) based on the outputted bounding box e.g., by expanding or contracting the outputted bounding box. In other examples, the face detection algorithms may output a partial or complete outline of the face, locations of the eyes and other features of the face, and the like. In these examples, the processor(s) may generate the bounding box 308 to cover the face area including the outline and features of the face.

At step 310, the processor(s) may detect eye positions in the identified face area 308, corresponding to a first eye 312A and a second eye 312B. For example, the processor(s) may execute an eye detection algorithm, as described with reference to the image capture and analysis component 132, to determine the eye positions. The processor(s) may generate an eye bounding box 314 that covers a rectangular area around the first eye 312A and the second eye 312B. The eye bounding box 314 may be specified by its width and height, and a corner (e.g., left-top) 315(1) of the rectangular bounding box, as described with reference to FIG. 2C.

At step 316, the processor(s) may determine positional measurements of the first eye 312A and the second eye 312B within the eye bounding box 314. The positional measurements may be based on features of the eyes identified by the eye detection algorithm e.g., pupils, center of nose bridge, corner of the eyes, and the like. For example, the positional measurements may include a first distance 320A (e.g., number of pixels) between pupil 318A of the first eye 312A and a center 320, a second distance 320B (e.g., number of pixels) between pupil 318B of the second eye 312B and the center 320, a third distance 322A (e.g., number of pixels) between the pupil 318A and a nearest vertical edge of the eye bounding box 314, a fourth distance 322B between pupil 318B and a nearest vertical edge of the eye bounding box 314, and/or an inter-pupil distance obtained as a sum of distances 320A and 320B. Other measurements between features of the eyes, and relative positions of the features within the eye bounding box are also envisioned.

At step 324, the processor(s) may determine if an eye image corresponding to the eye bounding box 314 satisfies criteria of the vision screening test(s) being administered. The criteria for an acceptable eye image may be based on requirements of further steps of the vision screening test(s). For example, the eye image may need to satisfy size and resolution requirements, requirements on positioning of the eyes in the eye image, and the like, so that features of the eyes being used for detecting diseases and/or deficiencies of the eyes are detectable in the eye image. Further details of the criteria and determination of whether the eye image satisfies the criteria at step 324 are described with reference to FIG. 3B. Step 324 may be performed on an image extracted from the oversampled image 304, corresponding to the area within the eye bounding box 314, or directly on the oversampled image 304 by accessing pixel values in the area corresponding to the eye bounding box 314.

At step 326 (step 324—No), the processor(s) may notify an operator of the vision screening device 104, e.g., via the user interface displayed on the display screen 122, that the eye image does not satisfy one or more of the criteria. In some examples, the notification may indicate that an eye image could not be found e.g., due to a failure of face detection and/or eye tracking algorithms. The notification may include information about the criteria not being satisfied and/or guidance to the operator for corrective actions e.g., indicating a direction of adjustment of positions of the device or the patient. Further details of step 326 are described with reference to FIG. 3B. In examples, the processor(s) may proceed to re-execute step 302 after the operator 102 re-positions the patient 106 and/or the vision screening device 104 in accordance with the guidance, to capture a new oversampled image after the adjustments are completed.

At step 328 (step 324—Yes), the processor(s) may execute the eye tracking and output generation component 136 to track the eyes using eye tracking algorithms known in the art, and maintain the eye image substantially unchanged from the eye image that satisfied the criteria of the vision screening test(s) at step 324. For example, due to small movements of the operator hand-holding the vision screening device 104 and/or small head movements of the patient 106 during the vision screening, the position of the eyes within the oversampled image 304 may change. The eye tracking and output generation component 136 may determine the eye bounding box 314 at a new location by specifying a new position of the corner (e.g., top-left) at 315(2), as described with reference to FIG. 2C. In instances where the eye tracking algorithms fail to locate and/or track the eyes, the workflow 300 may re-start at the step 302 by re-capturing an oversampled image, and continue the sequence of operations as shown. In some examples, if the failure to track the eyes continues for a threshold amount of time, the operator of the device may be notified e.g., by performing the operations of step 326.

At step 330, the processor(s) may execute the eye tracking and output generation component 136 to output a stabilized eye image which compensates for the small movements described above, and maintains the position of the eyes at substantially fixed positions within the stabilized eye image. The stabilized eye image is generated by extracting image data corresponding to the eye bounding box 314 area of the oversampled image 304. It may be noted that the size of the eye bounding box 314 image may also vary based on a distance between the vision screening device 104 and the patient 106. For example, the eye bounding box may be larger when the patient is closer to the vision screening device 104. In examples, the stabilized eye image 314 may be scaled to a fixed size (e.g., a fixed width and height) to provide a stable, flicker-free, and consistent display of the eye image to the operator.

Figure 3B:
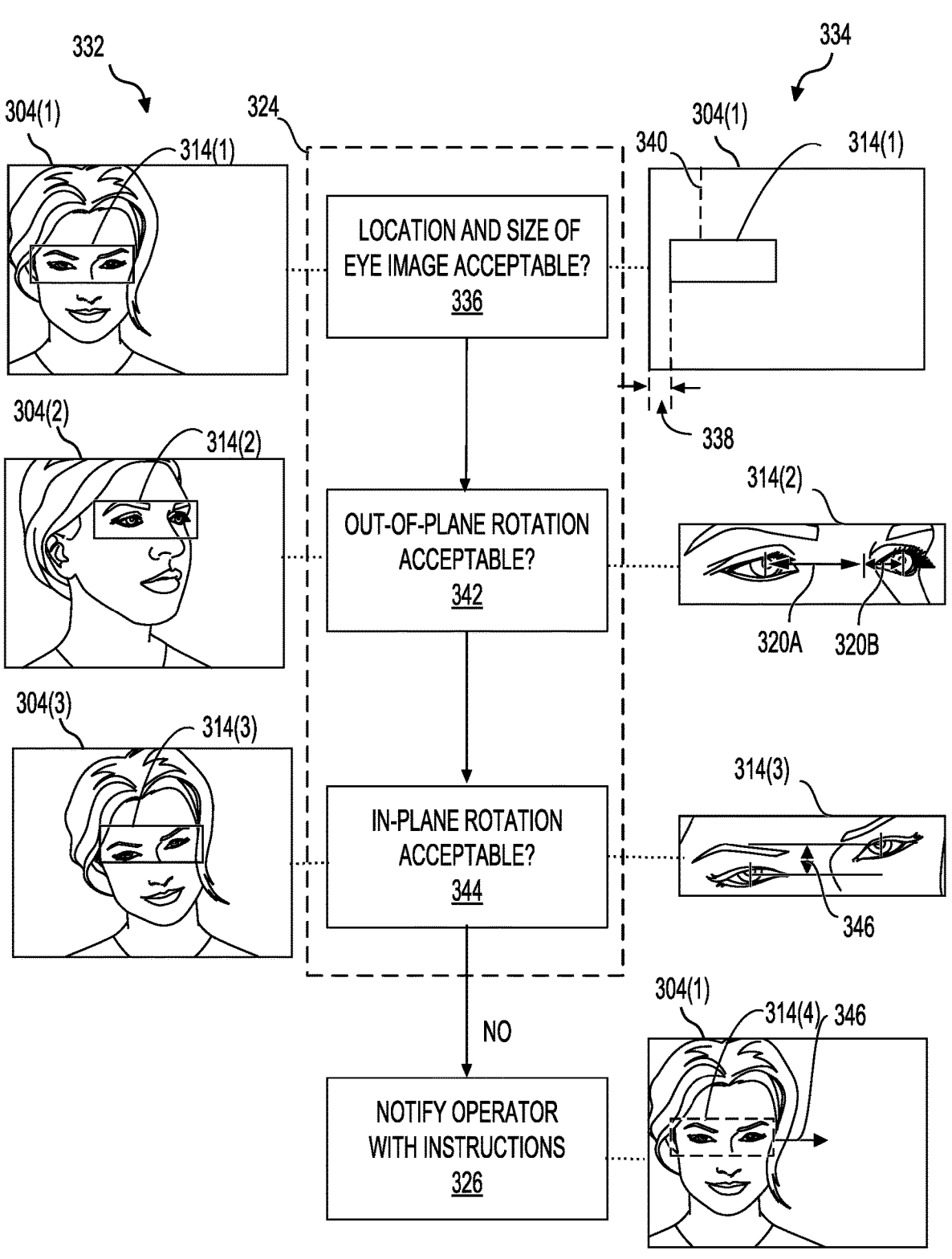
FIG. 3B provides a pictorial flow diagram of example validation steps, at step 324 of FIG. 3A, of an eye image captured during the vision screening test.

As discussed above, step 324 may determine whether the eye image indicated by the eye bounding box 314 satisfies one or more criteria. With reference to FIG. 3B, column 332 illustrates examples the oversampled image and corresponding eye bounding boxes, and column 334 illustrates the positional measurements related to specific criteria being tested at step 324. As discussed with reference to the eye image validation component 134, the eye image(s) may be required to have a minimum pixel resolution so that features of the eye(s) used to determine diseases and/or deficiencies of the eyes are detectable. At step 336, the eye image validation component 134 may check if size of the eye image (e.g., total number of pixels) is acceptable e.g., greater than a pre-defined minimum number of pixels. For example, if the patient is located at a distance beyond an operating distance of the vision screening device 104, the size of the eye image may be too small e.g., the number of pixels may be less than the minimum number of pixels.

The eye image validation component 134 may also check if location of the corresponding eye bounding box 314(1) relative to the oversampled image 304(1) is acceptable. If a top-left corner of the eye bounding box 314(1) is located at coordinates $(x_1, y_1)$ with respect to an origin $(0, 0)$ at the top-left corner of the oversampled image 304(1), then the distance 338 is $x_1$, and the distance 340 is $y_1$. The distances 338 and 340 (e.g., as a number of pixels) are indicative of distances of the eye bounding box 314(1) from the edge of the oversampled image 304(1). The eye image validation component 134 may determine the location of the eye image to be acceptable if the distance 338 and the distance 340 are each greater than a threshold distance (e.g., a threshold number of pixels). If the distance 338 and/or the distance 340 are less than the threshold distance, it indicates that the eye bounding box 314(1) is too close to the edge of the oversampled image, and small movements during the vision screening test may result in portions of the eyes not being captured in the oversampled image. In some examples, a distance 338 or 340 less than the threshold distance may indicate that portions of the eyes are already outside the oversampled image that is captured. The patient and/or the vision screening device may need to be moved in a direction so that the eyes of the patient move towards the center of the oversampling sensor 110 of the camera 108.

At step 342, which may be included in step 324, the eye image validation component 134 may determine if a level of out-of-plane rotation, if any, of the head of the patient relative to the vision screening device, is below an acceptable threshold. As an example, an eye image 314(2) may be generated from the oversampled image 304(2), which depicts a level of out-of-plane rotation of the patient's head that is greater than the acceptable threshold. This condition may be determined from the measurements 320A and 320B between pupils of the eyes and a center, as described with reference to FIG. 3A. In a scenario with none or minimal out-of-plane rotation, a ratio of 320A to 320B would be approximately equal to 1.0. The eye image validation component 134 may compute the ratio of 320A to 320B, and if the absolute difference between the ratio and 1.0 is more than a threshold fraction, the eye image validation component 134 may determine that the out-of-plane rotation is not acceptable. For example, if the threshold fraction is 0.1, an acceptable range of the ratio would be [0.9, 1.1].

At step 344, which may be included in step 324, the eye image validation component 134 may determine if a level of in-plane rotation, if any, of the head of the patient is relative to the vision screening device, is below an acceptable threshold. As an example, an eye image 314(3) may be generated from the oversampled image 304(3), which depicts a level of in-plane rotation of the patient's head that is greater than the acceptable threshold. This condition may be determined from measurement of vertical distance 346 between pupils of the first and second eye. In a scenario with none or minimal in-plane rotation, the distance 346 may be substantially zero. The eye image validation component 134 may compute a difference between y-coordinate values of the first and the second eye, and if the absolute difference is more than a threshold distance, the eye image validation component 134 may determine that the in-plane rotation is not acceptable, and acceptable otherwise. For example, if the first eye is centered at $(x_f, y_f)$ and the second eye is centered at $(x_s, y_s)$, the absolute difference $|y_f - y_s|$ may be compared with the threshold distance, which may be expressed as a number of pixels. In other examples, a ratio of the absolute difference of y-coordinates to an inter-pupil distance, (distance 320A+distance 320B), may be compared with a threshold ratio to determine acceptability. In some examples, the eye image validation component 134 may determine whether the in-plane rotation is acceptable, after applying a rotation compensation technique on the eye image 314(3) e.g., the threshold distance or the threshold ratio may indicate a maximum amount of in-plane rotation remaining after the rotation compensation technique is applied. In examples, the rotation compensation technique may rotate the bounding box corresponding to the eye image 314(3) within the oversampled image 304(3) until the distance 346 is reduced, or is substantially zero e.g., by applying an anti-clockwise rotation in the example shown.

If an eye image is found to be acceptable at each of the steps 336, 342, 344, the eye image may be determined to satisfy the criteria of acceptance at step 324, and the workflow 300 may proceed to step 328. Fewer or more validity criteria may be checked at step 324. For example, step 324 may include an additional step to determine if a sharpness level of the eye image is acceptable. As is known in art in the field of image processing, a sharpness of an image may be determined based on characteristics of edges detected in the image. Similar techniques may be used to determine a sharpness of the eye image, and compared with a minimum sharpness level.

If an eye image is found to be not acceptable at one or more of the steps 336, 342, 344, the eye image may be determined to not satisfy the criteria of acceptance at step 324, and the workflow 300 may proceed to step 326. At step 326, an operator of the vision screening device 104 may be notified, e.g., via the user interface displayed on the display screen 122, that the eye image does not satisfy one or more of the criteria, and an indication of which criteria are not satisfied. As described above, the notification may include guidance to the operator for corrective actions. For example, the processor(s) may use the display screen 122 to display, to the operator, a visualization of the oversampled image and the eye bounding box. The visualization may include a portion of the oversampled image, including the eye bounding box, wherein a color or other characteristic of the eye bounding box is indicative of an acceptable eye image, or particular criteria that are not satisfied by the eye image. As an example, eye image bounding box 314(4) may be determined to be not acceptable at step 336. In this example, a color and/or line style outlining the eye image bounding box 314(4) may indicate this determination at step 336. For example, the color of the outline of the eye image bounding box may be green if the eye image satisfies all criteria, but may change to yellow, orange, or red based on the eye image not satisfying one or more criteria. In some examples, the color may be indicative of the criteria not being satisfied. In some examples, the color of the outline may transition from green to yellow as the eye bounding box approaches one or more acceptability thresholds, before the thresholds area actually crossed. In addition, the processor(s) may display an indication of a corrective action on the display screen 122. In the example shown, an arrow 346 indicates that the patient and/or the vision screening device 104 needs to be moved so that the eyes of the patient move towards a center of the display. In other examples, arrows may indicate a direction of corrective action needed to remove unacceptable levels of in-plane and/or out-of-plane rotation (e.g., rotate patient's head to the left or right, clockwise or counterclockwise etc.).

As described above with reference to FIGS. 3A and 3B, eye images meeting acceptability criteria are extracted from oversampled images captured by the camera 108 of the vision screening device 104, and the eyes of the patient are tracked during the vision screening to output stabilized eye images by compensating for small movements. An operator of the vision screening device 104 may be presented with a visualization of the tracked eye bounding box indicating whether the eye image is meeting acceptability criteria of the vision screening test(s) being administered.

Figure 4:
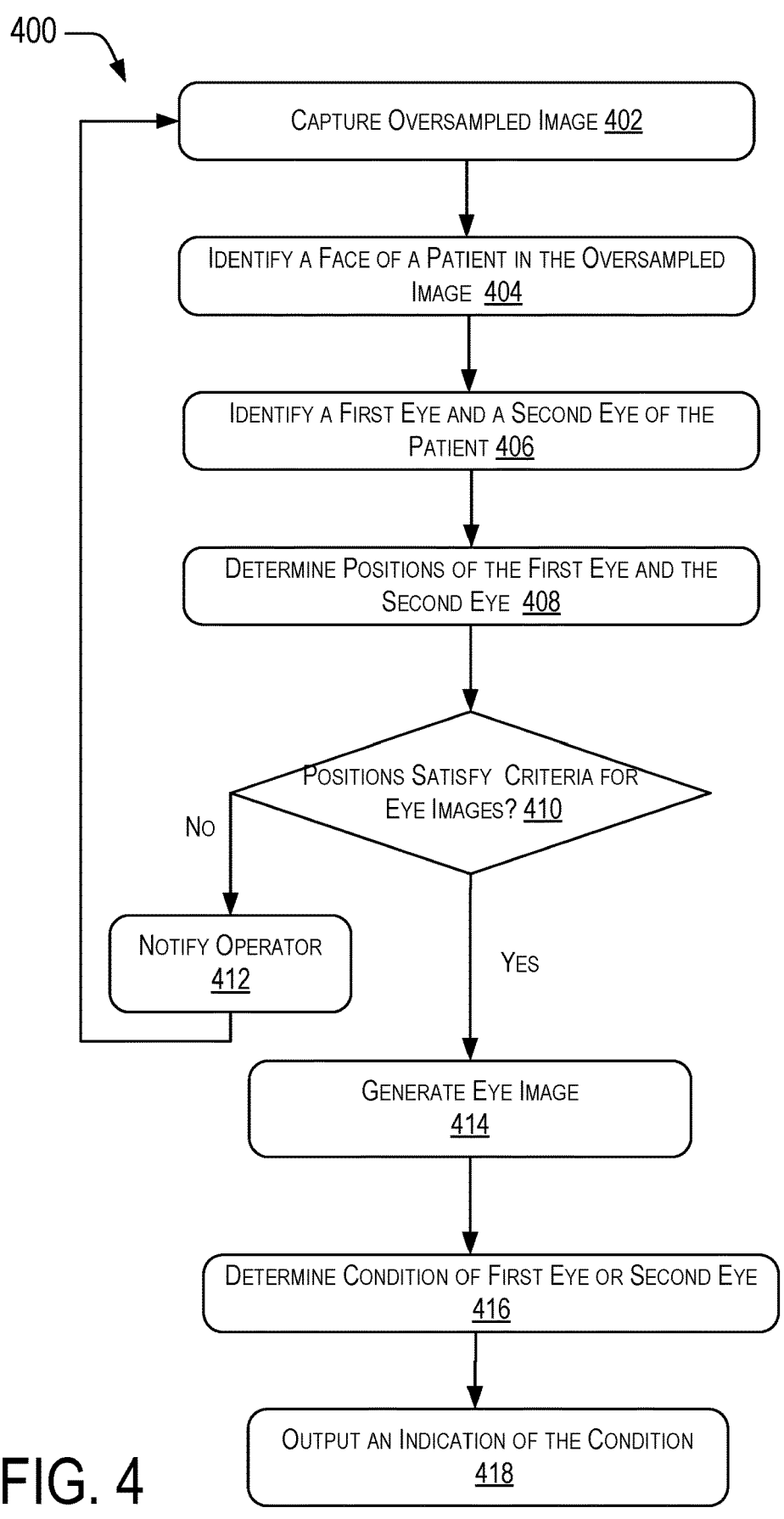
FIG. 4 provides a flow diagram illustrating an example method of the present disclosure.

FIG. 4 provides a flow diagram illustrating an example method for vision screening using the vision screening device, as described herein. The method in FIG. 4 is illustrated as a collection of blocks in a logical flow graph, which represents sequences of operations that can be implemented in hardware, software, or a combination thereof. In the context of software, the blocks represent computer-executable instructions stored on one or more computer-readable storage media that, when executed by processor(s), perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the method illustrated in FIG. 4. In some embodiments, one or more blocks of the method illustrated in FIG. 4 can be omitted entirely.

The operations described below with respect to the method illustrated in FIG. 4 may be performed by the device 104 or system 118 described herein, and/or by various components thereof. Unless otherwise specified, and for ease of description, the method illustrated in FIG. 4 will be described below with reference to the system 100 and the vision screening device 104 shown in FIG. 1. In particular, any of the operations described with respect to the method illustrated in FIG. 4 may be performed by the image capture and analysis component 132, the eye image validation component 134, the eye tracking and output generation component 136, and/or the patient screening component 138 executed by the processor(s) 128 of the vision screening device 104 and/or by the analysis component(s) 150 executed by the processor(s) 146 of the vision screening system 118, either alone or in combination.

With reference to the example method 400 illustrated in FIG. 4, at operation 402, the image capture and analysis component 132 and/or one or more processors associated therewith may cause a camera to capture an oversampled digital image of a patient and their surrounding environment. For example, the camera may comprise the camera 108 of the vision screening device 104, equipped with the oversampling sensor 110. The oversampling sensor 110 is configured to capture an oversampled image of the patient and their surrounding environment such that a target area comprising a portion of the oversampled area, such as the eyes of the patient, comprises a sufficient number of pixels (e.g., is of a sufficiently high resolution) for purposes of one or more vision screening test(s) being administered to the patient. The vision screening test(s) may have different distance requirements between the patient and the vision screening device. The camera 108 may be equipped with a lens with a field-of-view suitable for capturing oversampled images of the patient at different operating distances from the vision screening device 104, and a resolution (e.g., number of pixels) of the oversampling sensor 110 may be sufficient for operation at the farthest distance to the patient required by the vision screening test(s) enabled by the vision screening device 104. In some examples, the oversampled image may be captured under ambient illumination of setting of the vision screening e.g., an examination room.

At operation 404, the image capture and analysis component 132 may identify a face of the patient in the oversampled image captured at operation 402. The image capture and analysis component 132 may apply a face detection algorithm, as well-known in the art, to the oversampled image to determine a location of a face in the oversampled image. The location of the face may be determined as a bounding box around the detected face, and may include locations of features of the face, such as eyes and mouth, or an outline of the face.

At operation 406, the image capture and analysis component 132 may identify a first eye and a second eye of the patient. The image capture and analysis component 132 may apply an eye detection algorithm, as known in the art, to an area within the bounding box around the detected face, or a larger area that includes the area within the bounding box of the face. The eye detection algorithm may output locations (e.g., x,y coordinates) of centers of the eyes, and may also include locations of features of the eyes such as inner and outer corners of the eyes, and a center between the first eye and the second eye.

At operation 408, the image capture and analysis component 132 may determine positions of the first eye and the second eye. In some examples, the eye detection algorithm applied at operation 408 may produce locations of pupils of the eyes as part of the detection output, which may be used as the positions of the eyes. The positions of the eyes may also be approximated by the coordinates of the center of the eyes, as output by the eye detection algorithm. Alternatively, or in addition, the image capture and analysis component 132 may apply a pupil detection algorithm to areas detected as eyes by the eye detection algorithm. In some examples, the pupil detection algorithm may be based on images captured under illumination of different wavelengths, such as infrared or near-infrared radiation.

At operation 410, the eye image validation component 134 may determine whether positions of the first eye and the second eye satisfy criteria for eye images. The criteria for eye images may vary based on requirements of the vision screening test(s). The eye images may include both the first eye and the second eye, and the criteria may specify requirements for positions of the pupils of the eyes within the eye image, or a center of the first eye and the second eye within the eye image. As described with reference to FIG. 3B, these criteria may include a requirement for horizontal alignment of the pupils (e.g., in-plane rotation less than a threshold), equal spacing requirement from a center of the eye image (e.g., out-of-plane rotation less than a threshold), minimum number of pixels between the pupils (e.g., related to size of the eye image), and the like.

If the positions of the eyes do not satisfy criteria for eye images (Operation 410—No), the eye image validation component 132 may notify an operator of the vision screening device 104. As described with reference to FIG. 3B, the notification may include information regarding the criteria not satisfied, and/or guidance to the operator for corrective action. For example, the notification may comprise a visualization indicating satisfaction of criteria using color coding of a bounding box around the eyes, and include arrows indicating direction of correction. The notification may be displayed to the operator on a display screen of the vision screening device e.g., display screen 122. The operations may be re-set to operation 402 after corrective actions are completed.

If the positions of the eyes satisfy criteria for eye images (Operation 410—Yes), the eye tracking and output generation component 136 may generate an eye image. In examples, the eye tracking and output generation component 136 may generate the eye image by extracting image data from the oversampled image captured at operation 402 in an area comprising the first eye and the second eye. In addition, the eye tracking and output generation component 136 may track the positions of the eyes and update the eye image so that the relative positions of the eyes within the eye image remain substantially unchanged in response to small movements of the vision screening device or the patient. The eye tracking and output generation component 136 may generate an eye image that is stabilized by compensating for the small movements. For example, as described with reference to FIG. 2C, a bounding box around the eyes, indicating an area of the oversampled image corresponding to the eye image, may be tracked and updated in real-time, near real-time, or intermittently at pre-set intervals by maintaining a current location of a corner e.g., left-top, of the bounding box around the eyes.

At operation 416, the patient screening component 138 and additional components of the vision screening device 104 may utilize the generated eye image at operation 414, and other data comprising images and/or video data of the eye(s) captured under various illumination, to determine a condition associated with the first eye and/or the second eye of the patient. The condition may include diseases and deficiencies detected in pupils, retinas, and/or lenses of the eye(s) of the patient 106, such as ametropia, strabismus, and retinal conditions, and the like. In some examples, captured and/or generated images of the eyes may be used to assist the operator 102 or a clinician in diagnosing diseases and deficiencies of the eye(s) of the patient 106. As such, additional components of the vision screening device 104 may also automatically determine the condition of the eye(s) based on analysis of the images captured by the vision screening device 104 during the vision screening.

At operation 418, the patient screening component 138 may output an indication of the condition of the first eye and/or the second eye. A first indication may correspond to a scenario where the condition of the eye(s) represents a diseased or abnormal state, and may include a recommendation of additional screening, and/or a diagnosis of a disease or abnormality detected. The first indication may also include links to stored images, including eye images, images captured under illumination of different wavelengths, and/or generated visualizations. A second indication may correspond to a scenario where the condition of the eye(s) are determined to be normal, and the second indication may indicate that the patient has passed the vision screening, or that the patient's eye(s) appear normal and healthy.

As discussed, the example method 400 may be performed by the components of the vision screening device 104 executed by the processor(s) 128 of the device 104. The example method 400 illustrates operations performed during at least a part of a vision screening test administered to a patient (e.g., the patient 106) to determine diseases and/or deficiencies associated with the eye(s) of the patient based on images of the eye(s) captured under illumination of different wavelengths. In alternative examples, some or all of the operations of method 400 may be executed by processor(s) 146 of a vision screening system 118 that is connected to the vision screening device 104 via the network 116.

Based at least on the description herein, it is understood that the vision screening devices and associated systems and methods of the present disclosure may be used to assist in performing one or more vision screening tests, including test(s) to screen for diseases and/or deficiencies of the eye(s) of the patient, where the patient is located at different distances from the vision screening device, based on requirements of the vision screening test(s). The components of the vision screening device described herein may be configured to capture an oversampled image of the patient and the surroundings, locate the eyes of the patient, and generate a stabilized image of the eyes of the patient at different operating distances. The components may perform image processing techniques to detect faces, detect eyes and features of the eyes, track positions of the eyes, and extract image data from the oversampled images corresponding to eye images of the patient. In addition, the vision screening device may be configured to generate radiation of different wavelength bands to illuminate the eyes of the patient undergoing vision screening, capture image(s) of the eye(s) under different illumination conditions, determine conditions of the eyes, and generate an output indicating a diagnosis, recommendation or results of the vision screening test. The device described herein may be portable and/or hand-held, thereby allowing the device to be used for screening of patients in a variety of environments without requiring use of tripod mounting of the device, and providing a comfortable experience for the patient by compensating for small movements of the patient. The device may generate stabilized eye images of sufficient resolution for diagnosing conditions of the eyes, supporting vision screening tests requiring the patient to be positioned at different distances from the vision screening device.

The foregoing is merely illustrative of the principles of this disclosure and various modifications can be made by those skilled in the art without departing from the scope of this disclosure. The above described examples are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

As a further example, variations of apparatus or process limitations (e.g., dimensions, configurations, components, process step order, etc.) can be made to further optimize the provided structures, devices and methods, as shown and described herein. In any event, the structures and devices, as well as the associated methods, described herein have many applications. Therefore, the disclosed subject matter should not be limited to any single example described herein, but rather should be construed in breadth and scope in accordance with the appended claims.

What is claimed is:

1. A vision screening device, comprising:

a sensor configured to capture an image;

a processor operably connected to the sensor; and memory storing instructions that, when executed by the processor, cause the processor to:

cause the sensor to capture a first image of an environment including a patient at a first time;

identify a first portion of the first image corresponding to a face of the patient;

determine, based on the first portion, a second portion of the first image disposed at least partially within the first portion, wherein the second portion illustrates a first eye of the patient and a second eye of the patient;

cause the second portion to be displayed on a display screen;

determine a first position of the first eye within the second portion, and a second position of the second eye within the second portion;

determine whether the first position and the second position satisfy respective eye position criteria;

based on determining that the first position and the second position satisfy the respective eye position criteria, extract image data from the first image, wherein the image data:

includes data corresponding to the second portion, and excludes data corresponding to a remainder of the first image outside of the second portion;

generate, based on the image data, a second image illustrating the first eye and the second eye;

cause the sensor to capture a third image at a second time later than the first time;

determine a third portion of the third image, the third portion including the face of the patient;

identify a fourth portion of the third portion, the fourth portion including the first eye and the second eye; and cause the fourth portion without the third portion to be displayed on the display screen.

2. The vision screening device of claim 1, wherein the display screen is disposed within a housing of the vision screening device.

3. The vision screening device of claim 1, wherein the instructions further cause the processor to:

display, on the display screen and based on determining that the first position and the second position do not satisfy the respective eye position criteria, instructions indicative of at least one of:

a change in position of the vision screening device, a change in position of the patient, or an adjustment of a head of the patient.

4. The vision screening device of claim 1, wherein the instructions further cause the processor to:

determine, based on the second image, a condition of at least one of the first eye or the second eye; and display, on the display screen, an output indicative of the condition.

5. The vision screening device of claim 4, wherein the condition is associated with at least one of: a visual acuity, an abnormality, a disease, or normal vision.

6. The vision screening device of claim 1, wherein a resolution of the sensor is based at least in part on a maximum distance between the sensor and the patient during operation of the vision screening device.

7. The vision screening device of claim 1, wherein the criteria include one or more of:

a size of the first eye, a location of the first eye relative to a boundary of the first image, a location of the first eye relative to a boundary of the second portion, or a distance between the first eye and the second eye.

8. A method, comprising:

capturing a first image, the first image including a patient;

identifying a first portion of the first image, the first portion illustrating at least part of a face of the patient;

identifying a second portion of the first image disposed at least partially within the first portion, wherein the second portion illustrates a first eye of the patient and a second eye of the patient;

determining, based on the second portion and relative to a center point of the first portion, a first position of a pupil of the first eye and a second position of a pupil of the second eye;

determining whether the first position and the second position satisfy respective pupil position criteria;

based on determining that the first position and the second position do not satisfy the respective pupil position criteria, determining a modified second portion, wherein the first position and the second position satisfy the respective pupil position criteria within the modified second portion;

extracting image data from the first image, wherein the image data:

includes data corresponding to the modified second portion, and excludes data corresponding to a remainder of the first image outside of the modified second portion;

generating, based on the image data, a second image illustrating the first eye and the second eye;

determining, based on the second image, a condition of at least one of the first eye or the second eye; and outputting an indication of the condition via an electronic device.

9. The method of claim 8, wherein the first image is captured at a first time, the method further comprising:

capturing a third image at a second time later than the first time;

identifying a third portion of the second image, the third portion including the face of the patient;

identifying a fourth portion of the third portion, the fourth portion including the first eye and the second eye of the patient; and causing the electronic device to display the fourth portion without the third portion.

10. The method of claim 8, wherein the pupil position criteria include one or more of:

a location of a pupil of the first eye relative to a boundary of the first image, a location of the pupil of the first eye relative to a boundary of the second portion, a horizontal distance between the pupil of the first eye and a pupil of the second eye, or a vertical distance between the pupil of the first eye and the pupil of the second eye.

11. The method of claim 8, further comprising:

outputting, via the electronic device, an indication that the respective pupil position criteria are satisfied within the modified second portion.

12. The method of claim 8, further comprising:

generating, based on at least one of the respective pupil position criteria not being satisfied, instructions for adjustments of a position of the patient; and outputting, via the electronic device, the instructions.

13. The method of claim 8, wherein the condition is associated with at least one of: a visual acuity, an optical abnormality, an optical disease, or normal vision.

14. A system, comprising:

memory;

a processor; and computer-executable instructions stored in the memory and executable by the processor to perform operations comprising:

causing a sensor to capture a first image of a patient;

determining a first portion of the first image corresponding to a face of the patient;

determining a second portion of the first image having a boundary disposed at least partially within the first portion, wherein the second portion illustrates a first eye of the patient and a second eye of the patient;

determining a first position of the first eye relative to the boundary of the second portion, and a second position of the second eye relative to the boundary of the second portion;

determining whether the first position and the second position satisfy respective eye position criteria;

based on determining that the first position and the second position do not satisfy the respective eye position criteria, determining a modified second portion, wherein the first position and the second position satisfy the respective eye position criteria within the modified second portion;

extracting image data from the first image, wherein the image data excludes data, of the first image, from outside of the boundary of the modified second portion;

generating, based on the image data, a second image illustrating the first eye and the second eye; and determining, based on the second image, a condition of at least one of the first eye or the second eye.

15. The system of claim 14, wherein the condition is associated with at least one of: a visual acuity, an optical abnormality, an optical disease, or normal vision.

16. The system of claim 14, wherein the first image is captured at a first time, the operations further comprising:

causing the sensor to capture a third image at a second time later than the first time;

identifying a third portion of the second image, the third portion including the face of the patient;

identifying a fourth portion of the third portion, the fourth portion including the first eye and the second eye of the patient; and causing the fourth portion without the third portion to be displayed on a display screen.

17. The system of claim 14, the operations further comprising:

generating, based on at least one of respective eye position criteria not being satisfied, instructions for adjustments of a position of the patient or a position of the sensor.

18. The system of claim 14, wherein the eye position criteria include one or more of:

a location of the first eye relative to a boundary of the first image, a location of the first eye relative to a boundary of the second portion, or a distance between the first eye and the second eye.

19. The vision screening device of claim 1, wherein the image data is first image data, and the instructions further cause the processor to:

determine, based on the first position and the second position not satisfying the respective eye position criteria, a modified second portion, wherein the first position and the second position satisfy the respective eye position criteria within the modified second portion; and generate, based on second image data extracted from the first image within the modified second portion, a third image illustrating the first eye and the second eye.

20. The system of claim 14, wherein a resolution of the sensor is based at least in part on a maximum distance between the sensor and the patient.

\* \* \* \* \*